(12) United States Patent
Nozaki et al.

(10) Patent No.: US 10,087,410 B2
(45) Date of Patent: Oct. 2, 2018

(54) CELL CULTURING DEVICE, CULTURING VESSEL, AND HOLDING VESSEL

(71) Applicant: Hitachi, Ltd., Tokyo (JP)

(72) Inventors: Takayuki Nozaki, Tokyo (JP); Guangbin Zhou, Tokyo (JP); Masaharu Kiyama, Tokyo (JP); Taku Nakamura, Tokyo (JP); Shizu Takeda, Tokyo (JP); Ryota Nakajima, Tokyo (JP); Masakazu Sugaya, Tokyo (JP); Koichi Terada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 280 days.

(21) Appl. No.: 14/770,627

(22) PCT Filed: Mar. 25, 2013

(86) PCT No.: PCT/JP2013/058648
§ 371 (c)(1),
(2) Date: Aug. 26, 2015

(87) PCT Pub. No.: WO2014/155500
PCT Pub. Date: Oct. 2, 2014

(65) Prior Publication Data
US 2016/0017271 A1    Jan. 21, 2016

(51) Int. Cl.
*C12M 1/34*    (2006.01)
*C12M 1/00*    (2006.01)
(Continued)

(52) U.S. Cl.
CPC ............ *C12M 45/20* (2013.01); *C12M 23/48* (2013.01); *C12M 23/58* (2013.01); *C12M 41/14* (2013.01); *C12M 41/36* (2013.01); *C12M 41/48* (2013.01)

(58) Field of Classification Search
CPC ......... C12M 41/14; C12M 23/48; B01L 9/00; B01L 9/52
See application file for complete search history.

(56) References Cited

U.S. PATENT DOCUMENTS

2003/0203479 A1* 10/2003 Cecchi ................ C12M 23/48
                                                              435/303.1
2005/0260742 A1* 11/2005 Watanabe ................ B01L 9/52
                                                              435/287.3
(Continued)

FOREIGN PATENT DOCUMENTS

JP     2005-204545 A    8/2005
JP     2006-014675 A    1/2006
(Continued)

OTHER PUBLICATIONS

Keitaigata Teion Yuso Yoki 0 Kaihatsu shi Saisei Iryoyo Baiyo Saibo no Chokyori Yuso ni Seiko, [online], 2005, Hitachi Butsuryu News Release 2005 Nen (Heisei 17 Nen) Aug. 23, 2005 (Aug. 23, 2005), [searched on Apr. 9, 2013 (Apr. 9, 2013)], internet, <http://www.hitachi-hb.co.jp/news/2005/news- 20050823.html>.
(Continued)

*Primary Examiner* — William H. Beisner
(74) *Attorney, Agent, or Firm* — Mattingly & Malur, PC

(57) ABSTRACT

In culture vessels for producing biological samples, it is possible to prevent decrease in a temperature at the time of taking out the culture vessels from an automatic culture apparatus and during delivery of the culture vessels which have been taken out from the automatic culture apparatus. This invention includes a culture vessel 201 holding a biological sample therein, a heat storage portion 701 holding the culture vessel, and a heat insulation portion 601 surrounding the heat storage portion. The whole circumference or a part of 609, 610, and 611 of the heat insulation portion
(Continued)

601 is removable depending on an arrangement environment.

20 Claims, 21 Drawing Sheets

(51) Int. Cl.
*C12M 1/36* (2006.01)
*C12M 3/00* (2006.01)

(56) References Cited

U.S. PATENT DOCUMENTS

| | | |
|---|---|---|
| 2007/0245763 A1 | 10/2007 | Uchida et al. |
| 2008/0029247 A1* | 2/2008 | Nozaki ............... C12M 41/22 165/104.17 |
| 2009/0078395 A1 | 3/2009 | Nozaki et al. |
| 2011/0229962 A1 | 9/2011 | Mizutani et al. |

FOREIGN PATENT DOCUMENTS

| | | |
|---|---|---|
| JP | 2007-284137 A | 11/2007 |
| JP | 2008-39209 A | 2/2008 |
| JP | 2009-73513 A | 4/2009 |
| JP | 2010-098971 A | 5/2010 |
| JP | 2010-163207 A | 7/2010 |
| WO | 2010/044417 A1 | 4/2010 |

OTHER PUBLICATIONS

International Search Report PCT/JP2013/058648.

* cited by examiner

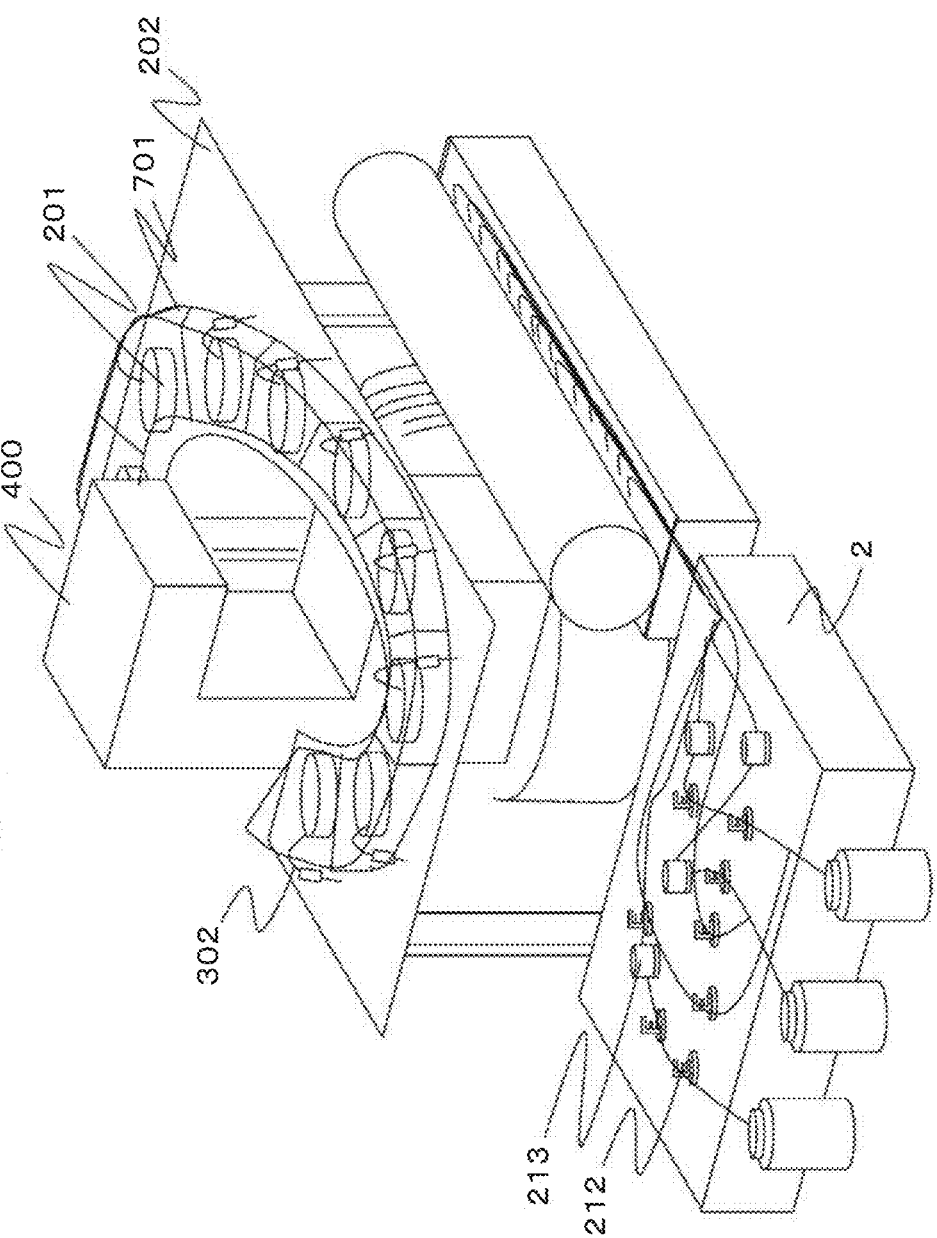

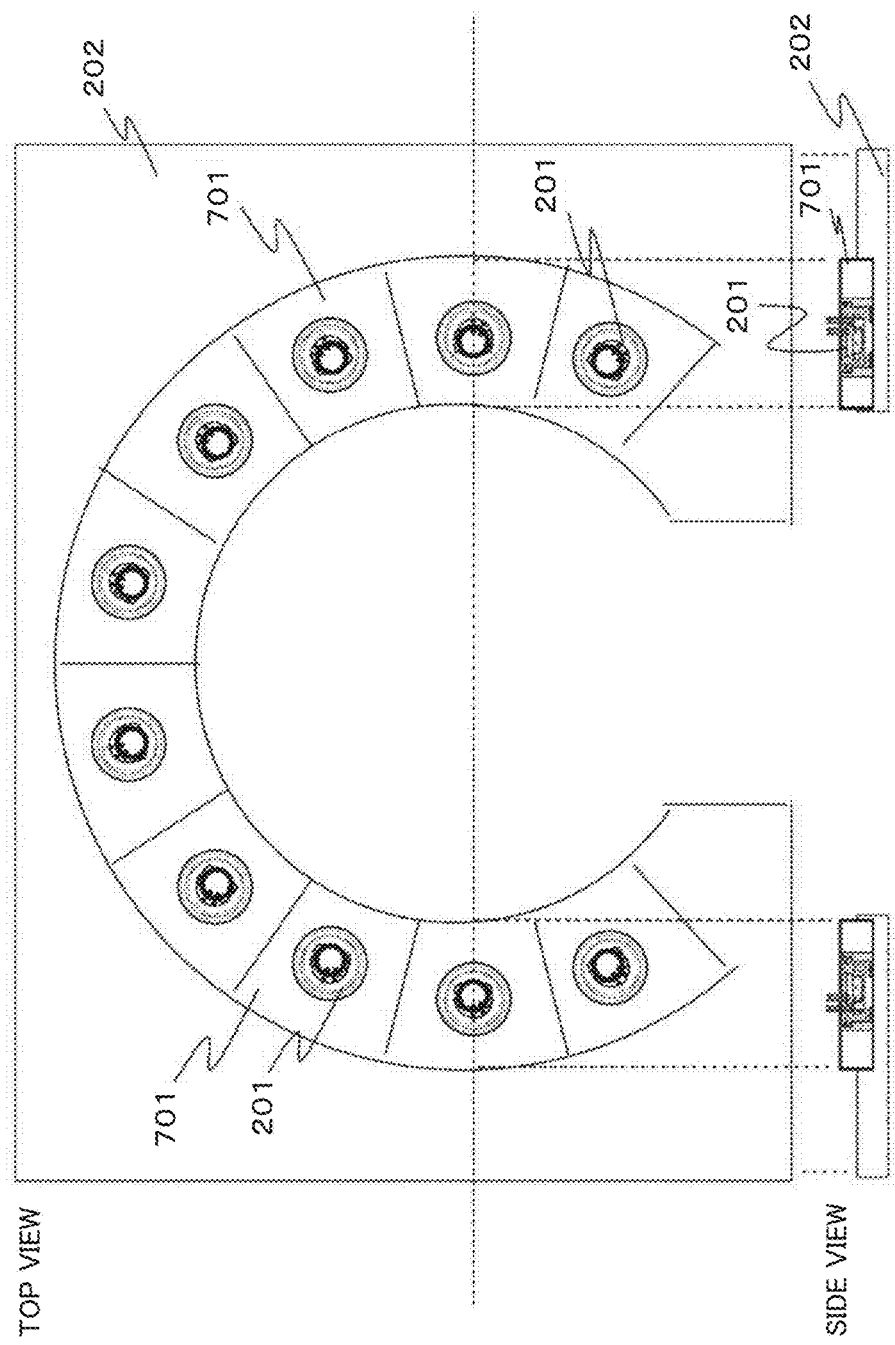

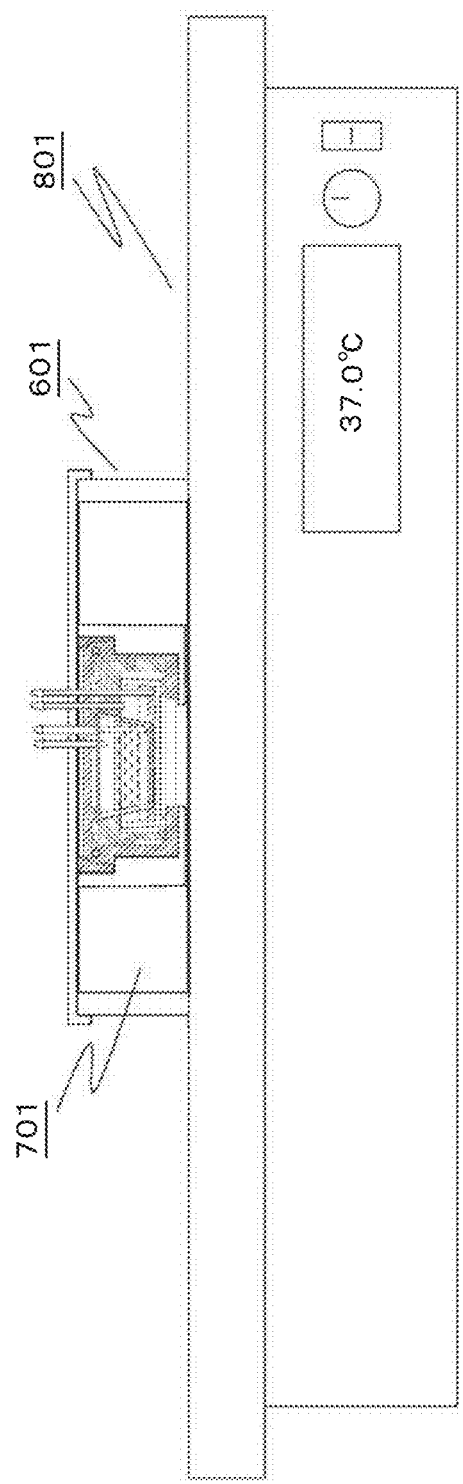

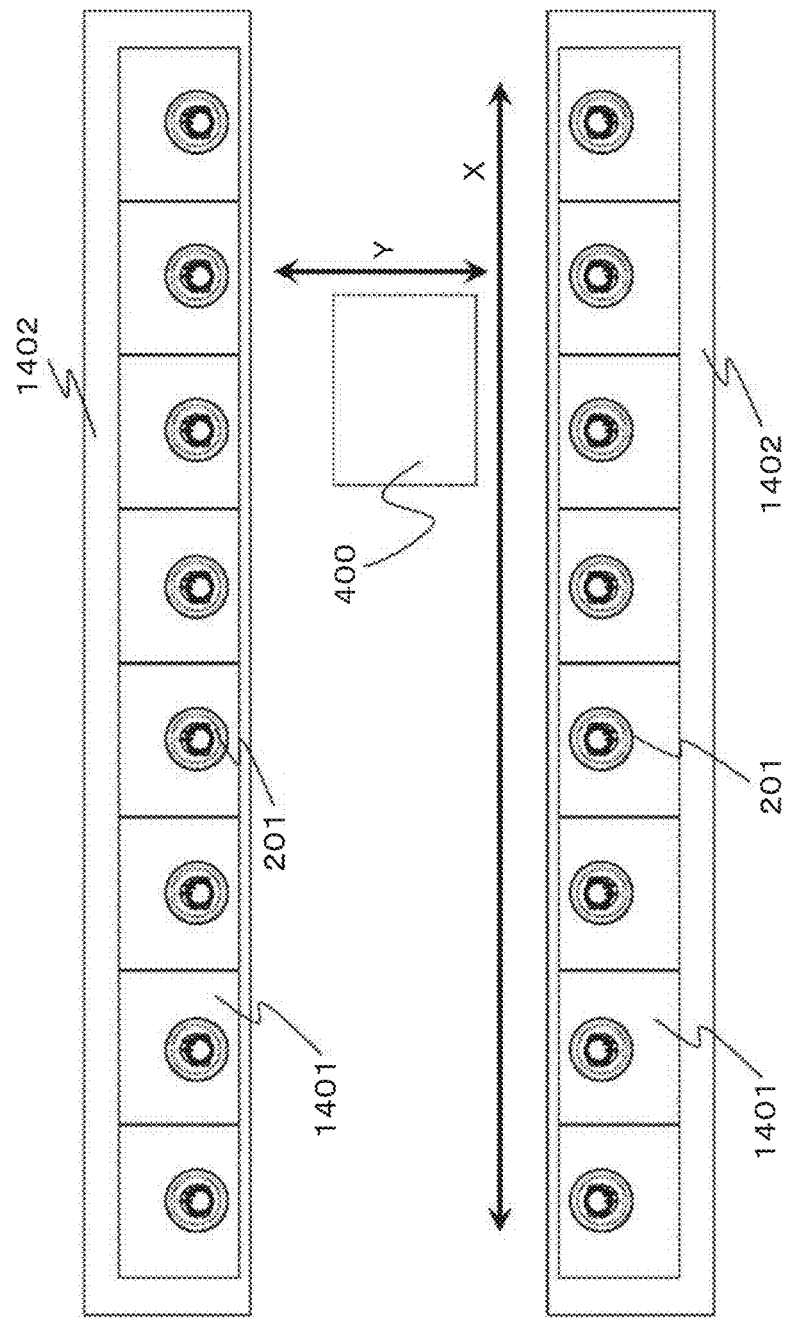

CELL CULTURING DEVICE, CULTURING VESSEL, AND HOLDING VESSEL

TECHNICAL FIELD

The present invention relates to a cell culture apparatus and relates to a technology for culturing cells or tissues by automatic operation and, after culture, delivering the cells or the tissues outside the cell culture apparatus.

BACKGROUND ART

Regenerative medicine for recovering functions of internal organs or the like with the use of biological samples such as regenerated tissues produced by using cells as a raw material is expected to be a radical treatment for diseases which could not have been conventionally cured. A production step of biological samples such as regenerated tissues complies with Good Manufacturing Practice (GMP) which is a standard of production management and quality control of medicine and the like. Production is performed in a Cell Processing Center (CPC) and complies with Standard Operating Procedure (SOP) which satisfies the GMP. Regarding the GMP, laws regulated by Ministry of Health, Labour and Welfare are enforced in Japan (e.g., Ordinance of the Ministry of Health, Labour and Welfare No. 179, Notification No. 480 of the Pharmaceutical Affairs Bureau). Outside Japan, related laws are enforced mainly in organizations in Europe and the Unite States (e.g., U.S. Food and Drug Administration, European Commission).

In order to reduce production costs of biological samples, an automatic culture apparatus for automating a part or all of culture steps has been required. Implementation of the culture steps by the automatic culture apparatus instead of manual operation achieves power saving and reduction of costs. This enables mass-production. In addition, because operation of the automatic culture apparatus is constant, contribution to stabilization of quality of produced regenerated tissues is also expected. After production, it is necessary to deliver regenerated tissues from the CPC which is a production location to an operating room in a medical institution for performing regenerative medical treatment. The CPC and the operating room are placed in the same site or are placed in difference locations. In any case, it is necessary to carry regenerated tissues in a space other than the production location and the treatment location, and, in the space, a temperature, cleanliness, and the like are not generally controlled.

For example, PTLs 1 and 2 are prior art literatures related to the above points. PTLs 1 and 2 disclose an apparatus for containing biological samples and transporting the biological samples while maintaining a temperature.

CITATION LIST

Patent Literatures

PTL 1: JP-A-2010-163207
PTL 2: JP-A-2007-284137

SUMMARY OF INVENTION

Technical Problems

As described above, in the case where biological samples produced by an automatic culture apparatus are applied to a living body for treatment, it is necessary to maintain the biological samples in a satisfactory state during production, transportation, and the like. In all steps of regenerative medical treatment, and, in particular, in a step of producing biological samples for transplantation with the use of a plurality of culture vessels, in order to perform shipping determination for determining whether or not transplantation is implementable, it is necessary to take out a culture vessel from the automatic culture apparatus for the shipping determination and check/evaluate quality of cells in the culture vessel on, for example, the day before transplantation. Although the inside of the automatic culture apparatus has a temperature (e.g., 37° C.) suitable for culture, the culture vessels are exposed to open air (e.g., 25° C.) when the culture vessel is taken out, and therefore a temperature of the culture vessels in which culture is continued, i.e., a temperature of the culture vessels which are not used for the shipping determination, may be reduced. Further, in a transportation step of taking out the culture vessels from the automatic culture apparatus after production and carrying the culture vessels to an operating room, there is also a risk that the temperature thereof may be reduced when the culture vessels are transported inside and outside the CPC. It means that a temperature condition is changed from a temperature condition which has been set at the time of production, and a state of the biological samples may be changed until transplantation. In particular, in the case where the biological samples are produced in the culture vessels having a temperature-responsive culture surface on which cell adhesion, cell spreading, and cell proliferation are enabled at 37° C. and cells spontaneously peel off at 32° C. or less, which is a phase transition temperature, and, when the temperature is reduced to be 32° C. or less during production and during transportation and cells peel off, quality of the biological samples is greatly changed. Therefore, it is important to maintain the temperature of the culture vessels from the production step and the transportation step until treatment is performed.

For example, the culture vessels are moved between rooms bypassing through a pass box. Further, a medium is exchanged for a medium for transportation in a safety cabinet and some processing is implemented as necessary. In addition, at the time of production, some culture vessels are taken out for examination from the automatic culture apparatus on, for example, the day before transplantation, and it is necessary to prevent decrease in a temperature of culture vessels for transplantation other than the culture vessels for examination. It is also necessary to take out the culture vessels for transplantation from an incubator on the day of transplantation, and therefore, similarly, the temperature may be reduced. After, transportation or the like, in the case where influence of transportation is evaluated with the use of a microscope, this evaluation is implemented at a room temperature. Therefore, similarly, the temperature may be reduced. In other words, when the culture vessels are taken out on the day before transplantation and the day of transplantation during culture, when the culture vessels are transported from the automatic culture apparatus to a transportation vessel after culture, and when observation is performed with the use of the microscope after transportation, it is necessary to maintain the temperature. This is particularly applicable to a case where the temperature-responsive culture surfaces are used in the culture vessels as described above. PTLs 1 and 2 disclose an apparatus for maintaining a temperature with the use of a transportation vessel in a transportation step, and therefore a temperature maintaining mechanism for use in steps other than the transportation step is further needed.

The invention has been made in view of the above problems, and an object thereof is to provide a cell culture apparatus, a culture vessel, and a holding vessel, each of which is capable of preventing decrease in a temperature from a production step and a transportation step until treatment is performed.

Solution to Problems

In order to achieve the above object, the invention provides a cell culture apparatus including: a culture vessel base which is arranged in a culture space and on which a plurality of culture vessels are placed; and a plurality of heat storage portions for warming the plurality of culture vessels, respectively, in which the plurality of heat storage portions, which are placed on the culture vessel base in the culture space during culture and contains the respective culture vessels, are provided so that at least one storage portion is removable from the culture space.

Further, in order to achieve the above object, the invention provides a culture vessel including: a heat storage portion surrounding the culture vessel for culturing a biological sample in warm the culture vessel; and a heat insulation portion surrounding an outer circumference of the heat storage portion, a part of the heat insulation portion being removable, in which the heat storage portion which is exposed by removing the part of the heat insulation portion can be heated.

Furthermore, in order to achieve the above object, in the invention provides a holding vessel, the holding vessel receives the plurality of culture vessels provided with a heat storage material and includes a heat insulation member surrounding the plurality of culture vessels provided with a heat storage material, each of the plurality of culture vessels including a heat storage portion surrounding the culture vessel to warm a cultured biological sample and a heat insulation portion surrounding an outer circumference of the heat storage portion, a part of the heat insulation portion being removable.

Advantageous Effects of Invention

According to a culture vessel provided with a heat storage material according to the invention, it is possible to prevent a temperature of the culture vessel from decreasing when the culture vessel is taken out from an automatic culture apparatus. Similarly, it is also possible to prevent the temperature from decreasing when the culture vessel taken out from the automatic culture apparatus is delivered and handled in a CPC or the like.

BRIEF DESCRIPTION OF DRAWINGS

FIG. 7A illustrates culture vessels provided with a heat storage material arranged in an apparatus according to Example 1.

FIG. 7B is a plan view illustrating a structure of culture vessels provided with a heat storage material according to Example 1.

FIG. 8 illustrates a state in which a vessel is placed on a hot plate according to Example 1.

FIG. 14 illustrates culture vessels provided with a heat storage material on a culture vessel base according to Example 3.

DESCRIPTION OF EMBODIMENTS

Hereinafter, various embodiments of the invention will be described with reference to drawings.

EXAMPLE 1

A basic structure and an operation flow of a cell culture apparatus according to examples including Example 1 will be described in detail with reference to the drawings. Note that a basic structure and an operation flow are not limited thereto, and an additional structure may be provided and the operation flow may be changed as appropriate in accordance with the use.

Figure 1:
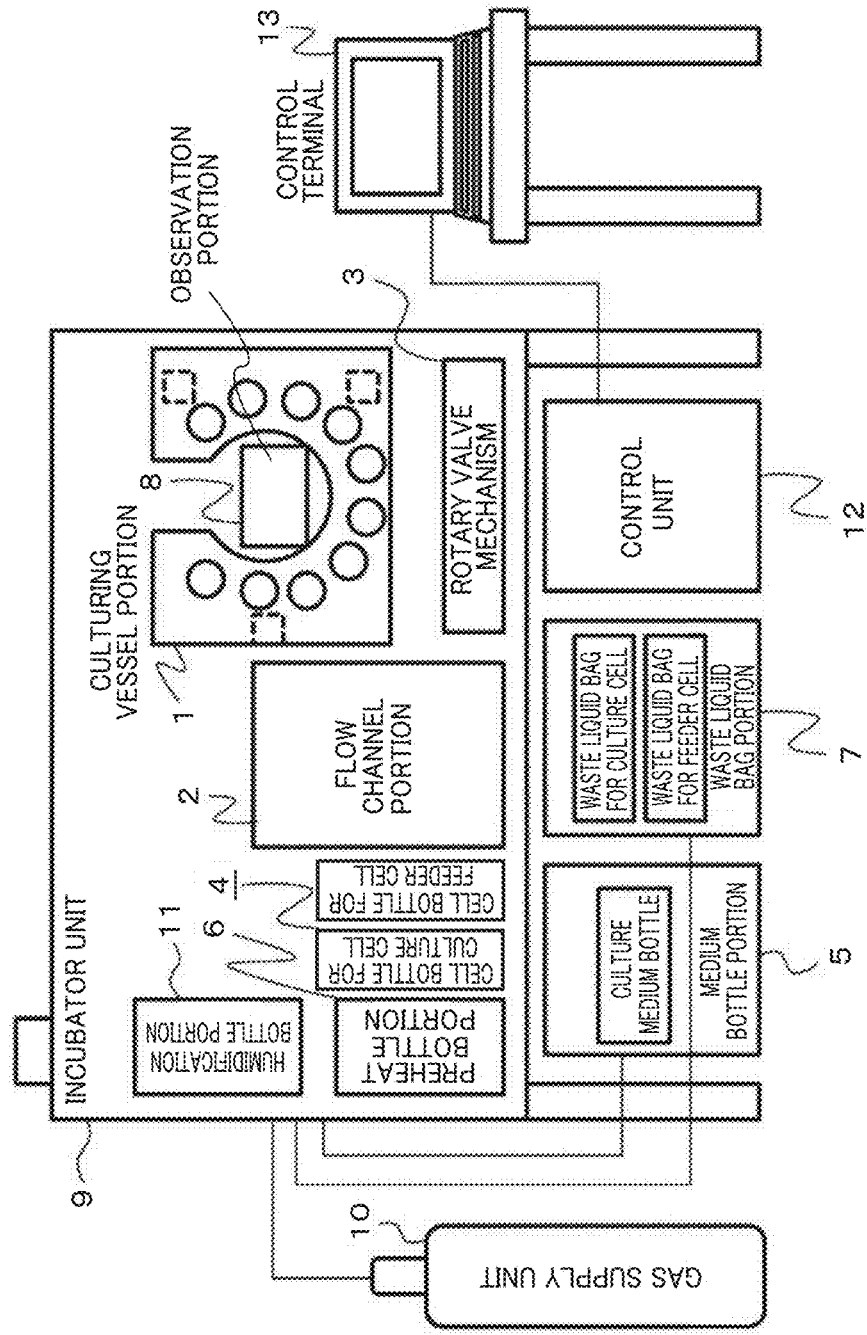
FIG. 1 illustrates a structure of an automatic culture apparatus according to Example 1.

As an example of a basic structure of an automatic culture apparatus, an automatic culture apparatus including twelve components will be described in detail with reference to FIG. 1. The twelve components are a culture vessel portion 1, a flow channel portion 2, a rotary valve mechanism 3, a cultured-cell and feeder-cell bottle portion 4, a medium bottle portion 5 including a refrigerator and the like, a preheating bottle portion 6, a waste fluid bag portion 7, an observation portion 8, an incubator unit 9, a gas supply unit 10, a humidification bottle portion 11, and a control unit 12. Note that, as illustrated in FIG. 1, the control unit 12 is provided with a control terminal 13.

In the automatic culture apparatus including the above components, the control unit 12 controls an electromagnetic valve, a tube pump, and the like (not illustrated) included in the flow channel portion 2 or the like of the apparatus, so that, in the closed-system flow channel which is a closed culture space, cells are seeded and are cultured in culture vessels of the culture vessel portion 1 with the use of a cell suspension and a medium in the cell bottle and the medium bottle arranged by a user.

Further, during cell culture, the control unit 12 controls the observation portion 8 including a microscope and the like provided in the apparatus, thereby capturing a cell image in the culture vessel. At times other than a time of automatically capturing a cell image, a time of cell seeding, a time of exchange of media, and a time of exchange of gas, it is possible to control a position of the microscope and capture and store a cell image on the basis of input via an operation screen of the control terminal by manually performing observation with the use of the microscope.

In the incubator unit 9 of the automatic culture apparatus, a temperature environment is observed by a sensor mechanism and observation results are displayed on the control terminal 13. All logs of operation of the electromagnetic valve, the tube pump, and the like of the flow channel portion and measurement are recorded in a storage unit (not illustrated) included in the control terminal 13, such as a hard disk. In addition, whether or not an operation error has occurred is determined, and an operation state is displayed on a monitor screen of the control terminal 13. Data thereof can be migrated to outside of the automatic culture apparatus.

Figure 2:
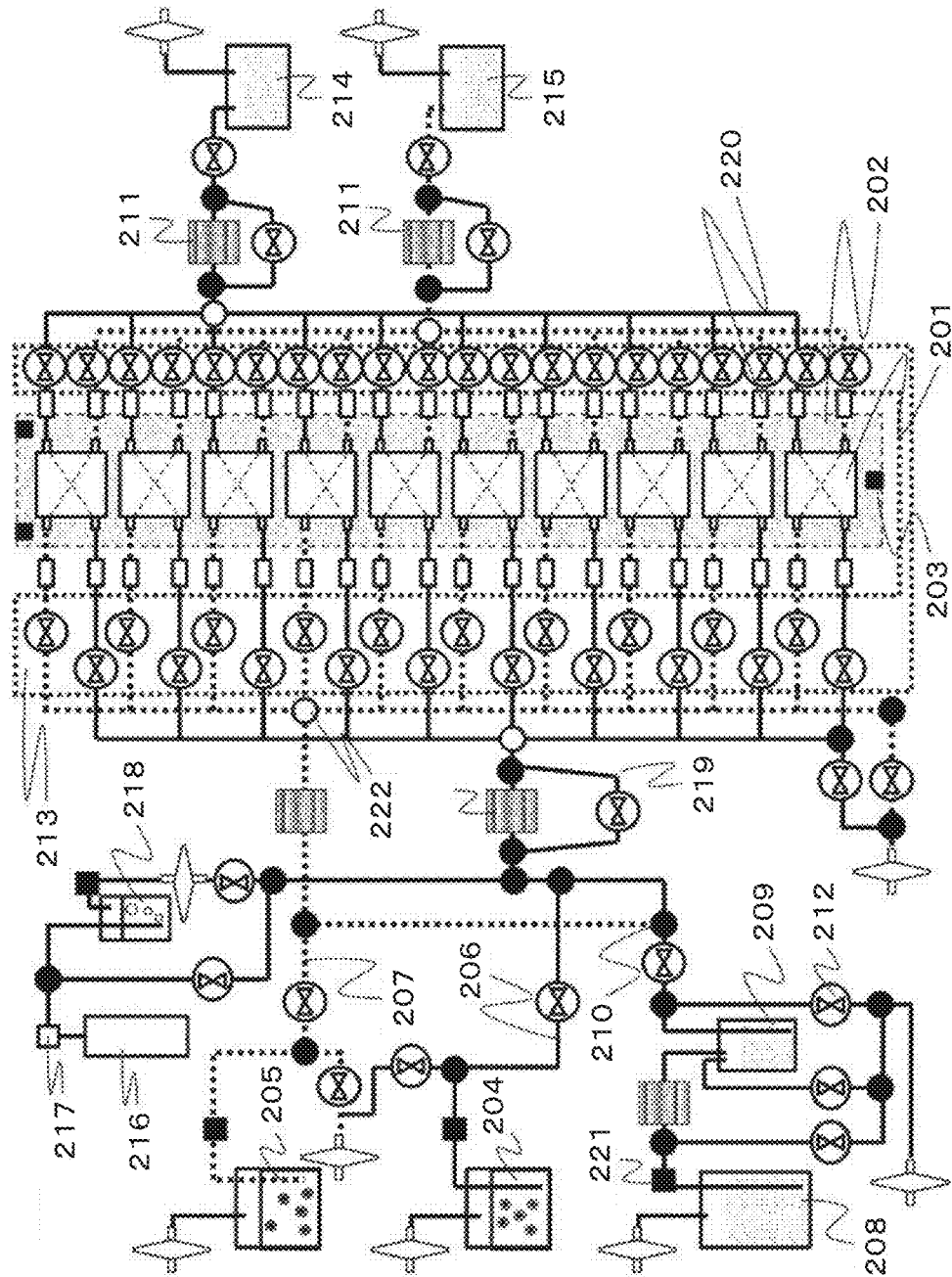
FIG. 2 illustrates a flow channel circuit of a closed-system flow channel of an automatic culture apparatus according to Example 1.

FIG. 2 illustrates a flow channel circuit of the closed-system flow channel of the automatic culture apparatus described above. The closed-system flow channel includes the culture vessel portion 1, the flow channel portion 2, the rotary valve mechanism 3, the cell bottle portion 4, the medium bottle portion 5, the preheating bottle portion 6, the waste fluid bag portion 7, the gas supply unit 10, and the humidification bottle portion 11 among the components illustrated in FIG. 1.

In Example 1, there will be described an example where regenerated tissues of epithelial cells such as corneal epithelial cells, oral mucosal epithelium cells, and epidermis cells are attempted to be produced. The kind of cell which can be cultured by the automatic culture apparatus is not limited thereto. In FIG. 2, the flow channel circuit is structured to use two kinds of cells because epithelial cells are a target to be cultured. However, in the case where only a single kind of cell is a target to be cultured, such as myocardial cells and fibroblasts, a flow channel circuit including a single cell bottle and a flow channel corresponding thereto may be structured. Alternatively, in the flow channel circuit structured to use two kinds of cells, only a flow channel circuit for a single kind of cell may be used. Further, although the flow channel circuit of FIG. 2 includes ten culture vessels, it is possible to use a flow channel circuit including a different number of culture vessels by arranging the culture vessels in parallel or removing the culture vessels.

The closed-system flow channel illustrated in FIG. 2 mainly includes the following components. In this example, in order to produce ten sets of regenerated tissues, ten culture vessels 201 are provided. All the culture vessels 201 are arranged on a culture vessel base 202 which is a planar plate, and an actuator 203 for changing inclination is attached to the culture vessel base 202.

Because two kinds of cells are used in this example as described above, two cell bottles 204 and 205 are used. Each of the two kinds of cells is introduced into a corresponding one of the cell bottles 204 and 205. In order to prevent mixing of the two kinds of cells in the culture vessels, all the culture vessels have a two-layer structure and culture the one kind of two cells in respective layers. The flow channel circuit from the cell bottles 204 and 205 to the layers of the culture vessels includes different flow channel circuits (1) and (2) in order to prevent cells from mixing in the middle of feeding fluid. A cell suspension in the cell bottle 204 is, for example, epithelial cells and is fed to a layer on one side of each culture vessel, for example, to upper layers of all the culture vessels via a solid-line flow channel circuit (1) 206. Meanwhile, a cell suspension in the cell bottle 205 is, for example, feeder cells and is fed to a layer on one side of each culture vessel, for example, to lower layers of all the culture vessels via a dotted-line flow channel circuit (2) 207. Separating flow channels on the basis of the kind of cell as described above prevents mixing of cells to be cultured in the upper layers of the culture vessels with cells to be cultured in the lower layers thereof. Because heterologously derived cells are used as the feeder cells, it is possible to eliminate a risk of xenotransplantation caused by mixing of heterologously derived cells into regenerated tissues to be transplanted. Note that, in FIG. 2, 222 denotes a multi-branch portion described below.

Although cell bottles are different depending on the kind of cell, the same medium is used, and therefore a single medium bottle 208 is used. The medium bottle is kept at 4° C. with the use of the refrigerator as described above with reference to FIG. 1. At the time of exchange of media, the medium having a necessary amount for exchanging gas once is moved to a preheating bottle 209, is heated to, for example, 36° C., and is then used for exchange of media. A flow channel from the preheating bottle appropriately branches to the flow channel circuit (1) 206 and the flow channel circuit (2) 207 via a two-branch portion 210. The medium fed to the flow channel circuit (1) 206 is sequentially fed to the layer on one side of each culture vessel. The same applies to the medium fed to the flow channel circuit (2) 207. A driving force for feeding fluid and supplying air in the flow channel is applied by a tube pump 211. A direction in which fluid is fed is controlled by an electromagnetic valve 212 and a rotary valve mechanism 213 corresponding to the rotary valve mechanism 3 of FIG. 1. At the time of exchange of media, an old medium which has been used for culture is fed to waste fluid bags 214 and 215.

During culture, oxygen and carbon dioxide are supplied to each culture vessel 201 as exchange of gas. This is because cells consume oxygen and discharge carbon dioxide. At the time of exchange of gas, in the apparatus, a gas cylinder 216 filled with air containing 5% $CO_2$ adjusts an air supply rate to a predetermined rate with the use of a gas flow meter 217, and then causes the air to pass through a humidification bottle 218 containing sterilized water to thereby saturate the air with moisture, and thus supplies the air. The air is supplied to each culture vessel via an air supply circuit 219 positioned in parallel with the tube pump 211.

Another structure of the flow channel circuit of this example includes sterilized detachable portions 220 and sterilized connection portions 221. The sterilized detachable portions 220 are arranged in flow channel tubes in the vicinity of the respective culture vessels 201. With this structure, it is possible to sterilely remove a single culture vessel to perform examination on, for example, the day before transplantation. The removed culture vessel, remaining culture vessels which have not been removed, and the flow channel can maintain sterility. On the day of transplantation, at the time of removal of the remaining culture vessels 201, the culture vessels 201 are removed with the use of the sterilized detachable portions 220. The sterilized detachable portion 220 is, for example, a heat-weldable flow channel tube, and two parts having a cutting portion in between are heat-welded and then the part therebetween is cut.

Meanwhile, the sterilized connection portions 221 are arranged in flow channel tubes in the vicinity of the cell bottles 204 and 205, the medium bottle 208, and the humidification bottle 218. The empty cell bottles 204 and 205, the empty medium bottle 208, and the empty humidification bottle 218 are carried into a CPC and are filled with a predetermined cell suspension, a predetermined medium, and a predetermined sterilized water, respectively, and are then attached to the closed-system flow channel by a user. At this time, the cell bottles 204 and 205, the medium bottle 208, and the humidification bottle 218 are sterilely connected via the sterilized connection portions 221.

Figure 3:
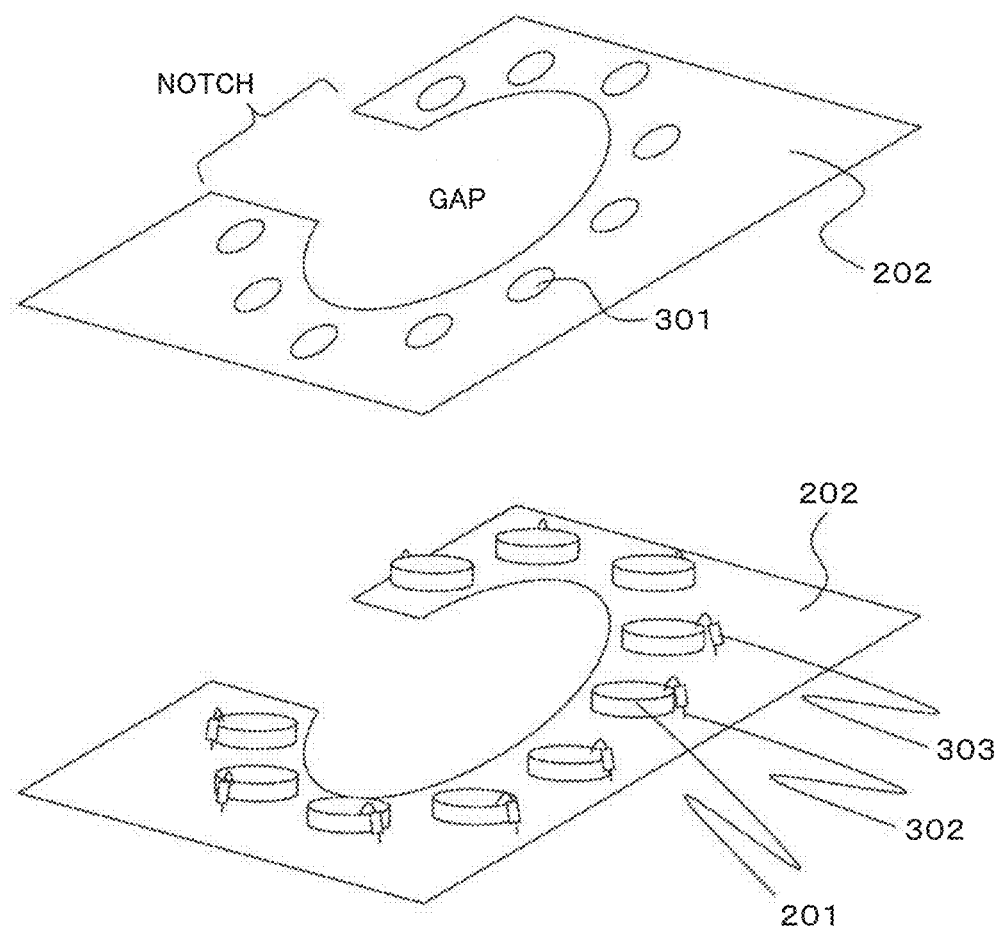
FIG. 3 illustrates an example of a culture vessel base included in a flow channel circuit according to Example 1.

FIG. 3 illustrates the culture vessel base 202 of the apparatus of this example and a state in which the ten culture vessels 201 are arranged on the culture vessel base 202. As illustrated in (A) on an upper side of FIG. 3, the culture vessel base 202 of this example has a shape of a horseshoe. That is, the culture vessel base 202 is shaped so that a central part of a rectangular plate is hollowed out to have an opening and a cutout is provided in an end of a side of the plate, the side being a side to be inserted into the apparatus, i.e., in apart of an outer circumference thereof. That is, the culture vessel base 202 has a so-called U shape. The inside of the central part of the culture vessel base 202 has a circular shape and the culture vessels 201 are arranged therearound in a circular shape. In the culture vessel base 202, holding means such as a recess for holding each culture vessel 201 is provided. In the hollowed circular opening part, the microscope of the observation portion 8 described below is provided. In locations where the culture vessels 201 are held, observation holes 301 for observation with the microscope are provided.

Because the culture vessel base 202 has the U shape as described above, an arrangement direction thereof in the apparatus is uniquely defined. That is, in the case where the culture vessel base 202 is arranged, the culture vessel base 202 is caused to approach the microscope from a cutout side provided on one side of the culture vessel base 202, thereby introducing the microscope into the opening, and then the culture vessel base 202 is attached to the actuator or the like. Because the culture vessel base 202 has this hollowed opening, it is possible to arrange the culture vessel base 202 at the center of the plurality of culture vessels 201. Further, because a user can easily arrange and remove the culture vessel base 202 without bringing the plurality of culture vessels 201 on the culture vessel base 202 into contact with the microscope, it is possible to prevent deterioration of quality of cell culture, the deterioration being caused by damage to the flow channel or the like due to human error.

Even in the case where, for example, a weight of the culture vessel base is heavy, arrangement work can be performed more easily in such a way that: a culture vessel arrangement base (not illustrated) having the same shape as that of the culture vessel base 202 or a plurality of divided culture vessel arrangement bases are provided in the apparatus; the culture vessels 201 and the like are arranged on the culture vessel arrangement base(s); and the culture vessel arrangement base(s) is(are) placed on the culture vessel base 202.

(B) on a lower side of FIG. 3 illustrates a state in which the ten culture vessels 201 are arranged on the culture vessel base 202. In this example, four gathered flow channel tubes 302 are connected to each of the culture vessels 201, and the four flow channel tubes 302 are arranged on outer side of the culture vessel base 202. Because the flow channel tubes 302 are arranged in an outer part of the culture vessel base 202, i.e., in an outer circumference thereof, it is possible to prevent deterioration of quality of cells caused by bringing the culture vessel base 202, the flow channel tubes, and the like into contact with the microscope at the time of driving the microscope. A sterilized detachable portion 303 to be used for removing a culture vessel is provided in the flow channel tubes in the vicinity of each culture vessel 201. With this, in the case where, on, for example, the day before transplantation, only one arbitrary culture vessel is removed to be used for shipping determination for determining whether or not cells have enough quality to be transplanted and is then evaluated, the removed culture vessel, culture vessels which have not been removed, and the flow channel can maintain sterility even after the culture vessel is removed.

In the case where, for example, a temperature-responsive cell culture insert vessel produced by CellSeed Inc. is used as a culture surface of the culture vessel and in the case where a temperature of the culture vessel 201 is reduced to be less than a phase transition temperature of the temperature-responsive culture surface, for example, less than 32° C., the hydrophobic temperature-responsive culture surface is changed to hydrophilic one, and cells which have been adhered, spread, and proliferated during culture at 37° C. spontaneously peel off. In the case where the cells peel off from the temperature-responsive culture surface due to decrease in the temperature, a culture condition is greatly changed, and therefore the quality of the cells is changed until transplantation. Therefore, in order to prevent a temperature of remaining culture vessels 201 after removal on the day before transplantation and a temperature in the inside of the incubator unit 9 from being decreased to be much less than 37° C., a small door is prepared on an upper part of a door of the incubator unit 9 to take out a culture vessel for quality check in a culture process on or before the day before completion of culture. Therefore, it is possible to reduce decrease in the temperature during work by reducing a time and an area for which/in which the inside of the incubator unit 9 is exposed to open air. In the case where the small door for taking out a culture vessel on the day before transplantation is made of a transparent material such as glass, it is also possible to check progress of culture through the small door, such as pH based on color of a medium and biological contamination based on turbidity.

When culture vessels are taken out on the day of transplantation, all the flow channel tubes connected to the culture vessels are sterilely cut, and then the plurality of culture vessels are removed from the apparatus in a state in which the culture vessels are arranged on the culture vessel base, and, after that, the culture vessels are carried to a safety cabinet or the like in a state in which the culture vessels are placed on the culture vessel base. That is, the plurality of culture vessels can be collectively treated. This makes it possible to prevent human error such as mislaying a culture vessel in the apparatus. Further, all the culture vessels can be taken out under the same time and temperature conditions.

Figure 4B:
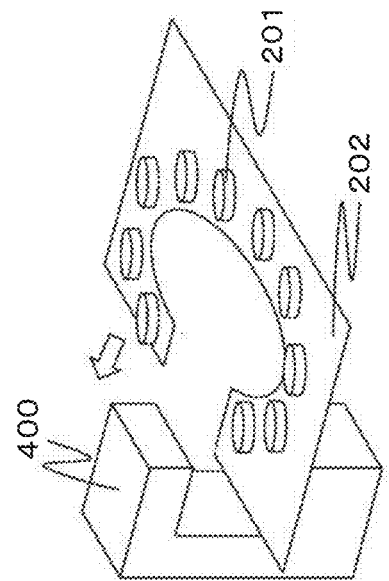
FIG. 4 illustrates a schematic example of an automatic culture apparatus according to Example 1.
Figure 4A:
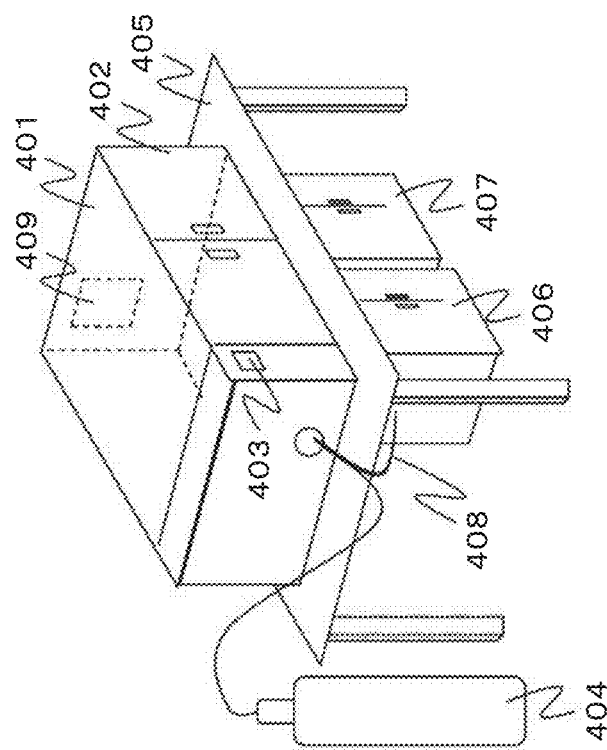

FIG. 4 is a perspective view schematically illustrating the automatic culture apparatus described above. As illustrated in (A) on a left side of FIG. 4, an incubator 401 is provided on a desk 405, and a refrigerator 406 keeping a medium bottle at, for example, 4° C. and a storage 407 keeping a waste fluid bag are provided under the desk. Note that the waste fluid bag may be arranged in the refrigerator 406. In that case, it is possible to reduce an arrangement area and costs. Note that (B) on a right side of FIG. 4 illustrates a relative positional relationship between a microscope 400 arranged in the observation portion 8 and the culture vessels 201, and the relative positional relationship will be described below.

The incubator 401 is connected to the refrigerator 406 and the storage 407 via a flow channel tube 408. This means that the incubator 401 maintaining a temperature at 37° C. and the refrigerator 406 maintaining a temperature at about 4° C. are not spatially close to each other and are separated by an air-conditioned space having generally about 25° C. in the CPC. With this structure, a high-quality heat insulation material is unnecessary between the incubator 401 and the refrigerator 406. This simplification of the structure of the apparatus can reduce costs and improve a temperature maintaining property.

The control unit 12 of FIG. 1 is arranged in the vicinity of the incubator 401 to operate the apparatus. In the case where a plurality of automatic culture apparatuses of this example are operated in parallel, all the automatic culture apparatuses are controlled by a single control device. Further, a control monitor for controlling the automatic culture apparatus from the outside of the CPC is arranged as necessary. A monitor is denoted by 403. Note that a small window 409 is arranged on a side surface of the incubator 401 and a role thereof will be described below.

Components (not illustrated) in the apparatus such as the flow channel portion 2 and the culture vessel base 202 arranged in the incubator 401 are placed on a mounting table (not illustrated) connected to a rail arranged in the incubator 401, and therefore it is possible to collectively draw out the components through a door 402. In the case where a user arranges a flow channel in the flow channel portion so that the flow channel is connected to the flow channel portion or the like at the time of start of culture, it is possible to arrange the flow channel in a state in which the mounting table is drawn out. This makes it possible to reduce complexity of arrangement of the flow channel and prevent human error caused by the user. At this time, it is desirable that the microscope arranged in the flow channel portion 2 and the observation portion 8 be not completely removed from the incubator 401 but be partially removed therefrom. Alternatively, the microscope may be fixed in the apparatus. This fixation is performed to prevent the microscope from being broken and a worker from being injured by fall of the microscope because the flow channel portion and the microscope are not light. Note that the flow channel portion 2 and the culture vessel base 202 may be removed from the incubator 401 and the microscope 400 may not be removed. In this case, the number of elements to be drawn out is reduced, as compared with the above method. This makes it possible to draw out the components more easily.

In the case where the so-called U-shaped culture vessel base 202 is used as in this example, as indicated by an arrow in (B) on the right side of FIG. 4, the culture vessel base 202 is inserted into a housing of the apparatus from the cutout side provided in the culture vessel base 202 through the door 402 illustrated in (A) on the left side of FIG. 4. This is because the microscope 400 is introduced into the opening without bringing the microscope 400 into contact with the culture vessel base 202.

Figure 5:
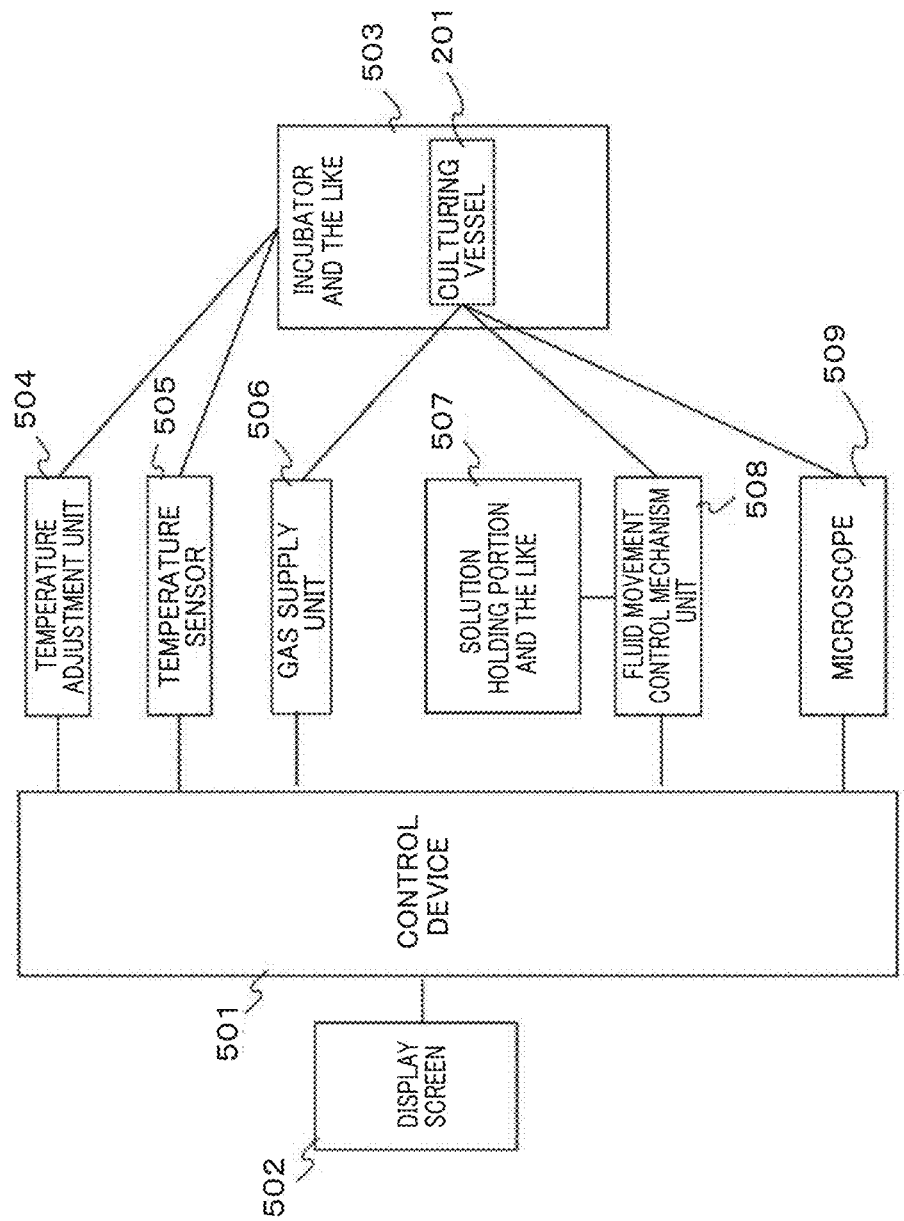
FIG. 5 is a block diagram showing a control mechanism of an automatic culture apparatus according to Example 1.

An example of a control mechanism of the automatic culture apparatus described above in this example will be described. FIG. 5 is a functional block diagram showing a functional configuration of the automatic culture apparatus described above. Components controlled by a control device 501 corresponding to the control unit of FIG. 1 are provided in an incubator unit/refrigerator/storage 503 and are connected to the culture vessels 201. Note that it is needless to say that the culture vessels 201 arranged in the automatic culture apparatus are provided in the incubator/refrigerator/storage 503.

In FIG. 5, the control device 501 is connected to a temperature adjustment unit 504 for controlling a temperature of the incubator/refrigerator/storage 503, a temperature sensor 505, a gas supply unit 506 which corresponds to the above gas supply unit 10 and supplies gas into the culture vessels, a cell bottle/medium bottle/preheating bottle/waste fluid bag 507, a fluid movement control mechanism unit 508 for automatically feeding fluid and gas in the flow channel corresponding to the above flow channel portion 2, and a microscope 509 corresponding to the above microscope 400 for observing cells.

The control device 501 and a display screen 502 corresponding to the above-mentioned control unit 12 and control terminal 13 respectively correspond to a processing unit and a storage unit and a display unit of a display device of a general computer which includes the processing unit including a CPU (Central Processing Unit), the storage unit, the display device, an input/output portion including a keyboard, and the like. The control device 501 causes the CPU serving as the processing unit to operate various programs stored in the storage unit. With this, the temperature adjustment unit 504, the temperature sensor 505, the gas supply unit 506, the fluid movement control mechanism unit 508, the microscope 509, and the solution holding portion/waste fluid bag 507 control a cultural environment in the incubator/refrigerator/storage 503. Therefore, it is possible to implement a predetermined culture step in the culture vessel 501.

Figure 6A:
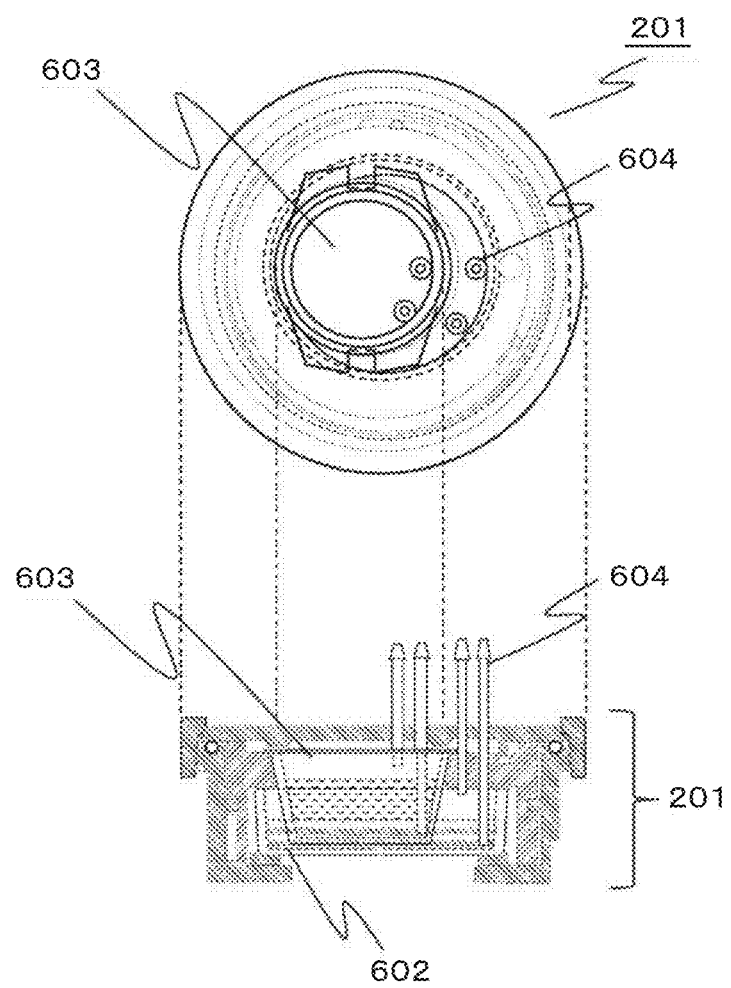
FIG. 6A illustrates a structure of a culture vessel according to Example 1.

Basic components of the culture vessel provided with a heat storage material according to Example 1 will be described with reference to FIG. 6A and FIG. 6B. The culture vessel 201 holds a biological sample therein. Therefore, it is possible to achieve sterilization by sterilization processing. In the case where the culture vessel 201 is made of, for example, polystyrene, it is possible to achieve sterilization before use by performing sterilization operation such as γ radiation or ethylene oxide gas processing. Although polystyrene has been exemplified in the above description, it is needless to say that any material can be used as long as the material is harmless to a biological sample and can be sterilized.

The culture vessel 201 is desirably a closed-system culture vessel forming a closed space. In this example, the culture vessel 201 indicates a culture vessel which includes a culture dish 602 and a temperature-responsive cell culture insert vessel 603 which are generally used for cell culture by manual operation and forms a closed space. By using two kinds of components, i.e., the culture dish 202 and the temperature-responsive cell culture insert vessel 203, it is possible to achieve two-layer culture of epithelial cells and feeder cells. In the case of automatic culture, culture is performed in a state in which the culture vessel is constantly connected to the flow channel circuit via the flow channel tubes. The flow channel tubes are attached to connectors 604 included in the culture vessel 201. Because the two-layer culture is performed in this example, supply and discharge connectors are arranged in each of the two layers. Therefore, four connectors in total are provided.

Figure 6B:
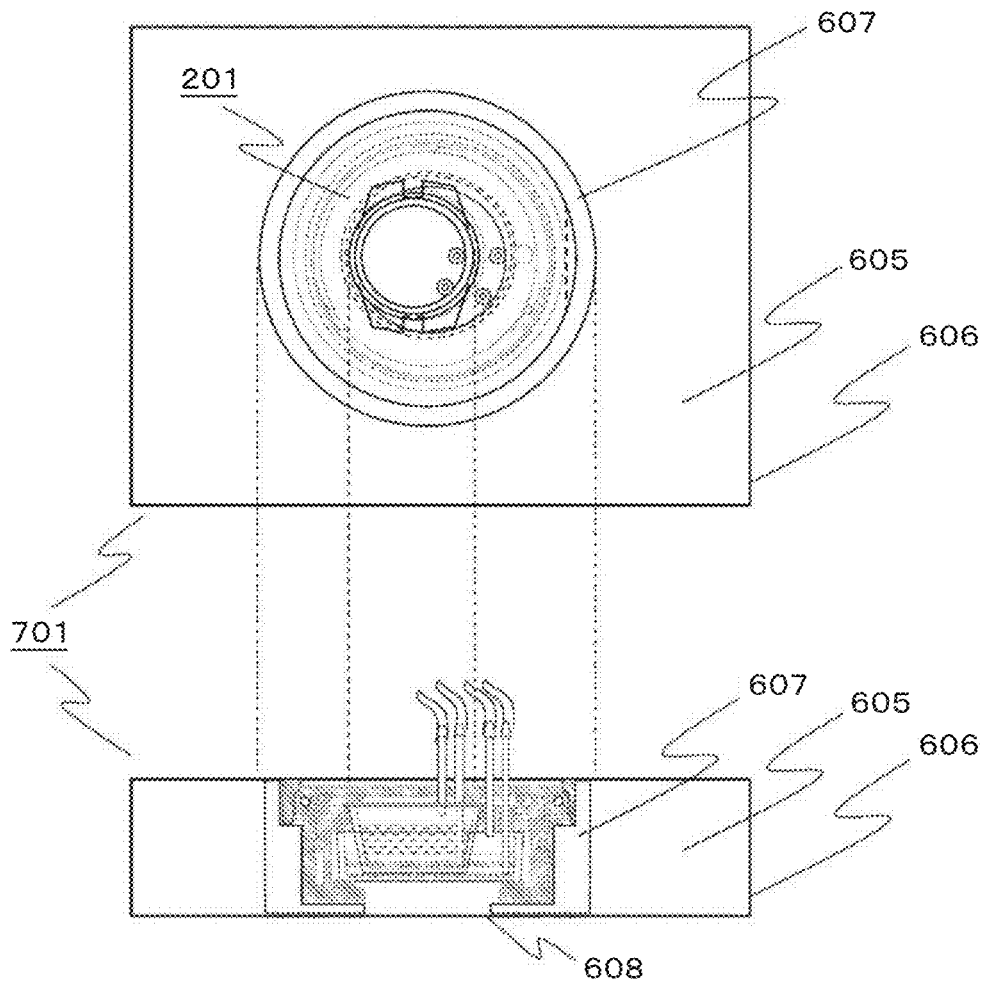
FIG. 6B illustrates a structure of a culture vessel provided with a heat storage material according to Example 1.

As illustrated in FIG. 6B, the culture vessel is surrounded by a heat storage portion 701 during culture. The heat storage portion 701 of this example includes a heat storage material 605, a heat storage portion vessel 606 which contains the heat storage material 605 and is made of polycarbonate, and a receiving portion 607 which is in contact with the culture vessel and is made of metal such as aluminum having high thermal conductivity. The receiving portion 607 efficiently conducts heat to the culture vessel 201 from the heat storage material 605 in the heat storage portion 701. A window 608 is provided to observe cells in a state in which the culture vessel 201 is provided in the heat storage portion 701. A bottom surface of the culture vessel 201 is exposed and therefore allows light to pass therethrough. The culture vessel 201 may be surrounded by a transparent material such as polyethylene instead of the window as long as an optical condition for observing cells has no problem. In this case, the culture vessel 201 is not exposed, and therefore decrease in a temperature becomes slower. Further, surrounding the culture vessel 201 with a transparent material can be easier than arranging a window.

In the case where a delivery time after culture is short, for example, about 1 hour, the heat storage material 605 may be any material as long as the heat storage material 605 is a substance having a high thermal capacity. The heat storage material 605 only needs to maintain a temperature until delivery is completed and, for example, needs to maintain a temperature of 34° C. or more under a room temperature (about 25° C.) for 1 or more hours. In this case, for example, it is assumed that the CPC and an operating room are placed in the same site. The heat storage material 605 is, for example, a solid heat storage material (e.g., heat storage material produced by MITSUBISHI CABLE INDUSTRIES, LTD).

In the case where a transportation time after culture is long, for example, in the case where the culture vessel is transported to a distant place by airplane, the temperature maintaining function for several days is needed. In that case, the heat storage material 605 is preferably a pure substance having a certain melting point or a substance having a large thermal capacity and a small temperature change in a melting point (e.g., ±1° C. or less). This is because, in the case where the melting point falls within a temperature range at the time of transportation, the thermal capacity during transportation is further increased. Further, a change in an internal temperature during transportation becomes small, and therefore influence of the temperature on a biological sample becomes small.

An example of the heat storage material 605 is hydrocarbon which is a pure substance. For example, a melting point of hydrocarbon (n-eicosane) having a chemical formula of $C_{20}H_{42}$ is 36.4° C. Hydrocarbon having a different carbon number has a different melting point. Therefore, by selecting the kind of hydrocarbon, it is possible to change a temperature that a cell transportation vessel constantly maintains. Note that, in the case of a fluid heat storage material such as hydrocarbon in particular is used, an airtight vessel which does not leak the fluid heat storage material to outside is needed. Meanwhile, in the case of the solid heat storage material, airtightness is unnecessary, and therefore it is possible to reduce costs.

After culture, in the case of the closed-system culture vessel, the closed-system culture vessel is sterilely removed from the flow channel circuit and is then carried while the closed state is maintained. In the case of using an open-system culture vessel whose cover is easily opened and closed, the cover is opened and closed in a state in which cleanliness in the automatic culture apparatus is maintained at a grade A which is equal to that in the safety cabinet and exchange of media or the like is operated during culture. After culture, a culture vessel is taken out from a culture portion once and is covered with a Parafilm or the like in order to prevent an internal medium from leaking. Then, the processing proceeds to the next step. Because the closed-system culture vessel is assumed to be used in this example, the processing can proceed to the next step without removing the culture vessel from the heat storage portion.

Figure 6C:
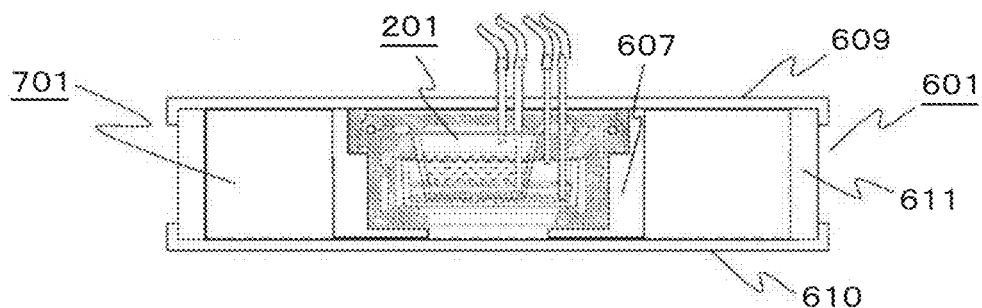
FIG. 6C illustrates another structure of a culture vessel provided with a heat storage material according to Example 1.
Figure 6D:
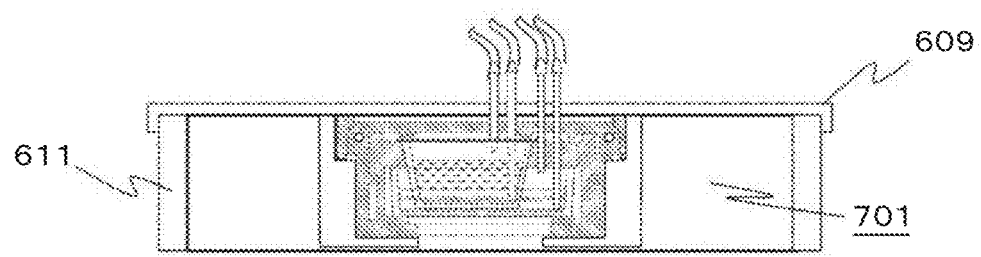
FIG. 6D illustrates another structure of a culture vessel provided with a heat storage material according to Example 1.
Figure 6E:
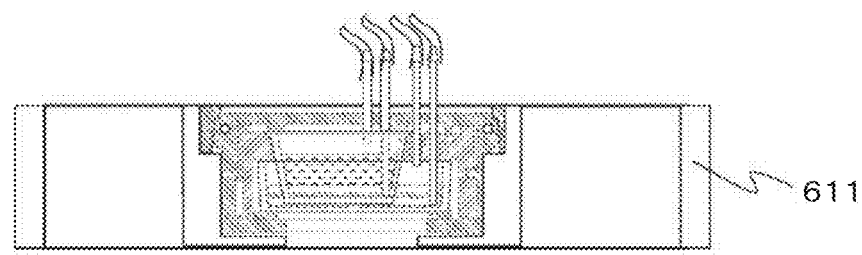
FIG. 6E illustrates another structure of a culture vessel provided with a heat storage material according to Example 1.
Figure 6F:
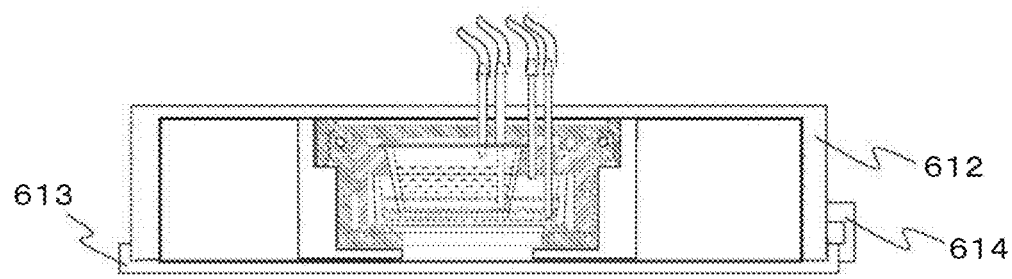
FIG. 6F illustrates another structure of a culture vessel provided with a heat storage material according to Example 1.

As illustrated in FIG. 6C to FIG. 6F, in the case of the culture vessel provided with a heat storage material of this example, the heat storage portion 701 is covered with a heat insulation portion 601 after culture. As illustrated in FIG. 6C, the heat insulation portion 601 includes an upper-surface heat insulation portion 609, a lower-surface heat insulation portion 610, and a side-surface heat insulation portion 611. The heat insulation portion 601 can be partially removed in accordance with a step, as illustrated in FIG. 6D and FIG. 6E. Further, a part of the heat insulation portion 601 may be integrally provided in accordance with the use, and FIG. 6F illustrates a culture vessel provided with a heat storage material in which an upper-surface and side-surface heat insulation portion 612 and a lower-surface heat insulation portion 613 are connected via a hinge 614.

A function and a structure of a culture vessel provided with a heat storage material of this example for use in culture in the automatic culture apparatus will be described with reference to FIG. 7A and FIG. 7B. As illustrated in FIG. 1 and FIG. 4, the automatic culture apparatus includes, for example, the incubator 401 which is a space for culturing cells at a culture temperature of 37° C., the refrigerator 406 keeping the medium bottle, the storage 407 receiving the waste fluid bag, a gas cylinder 404, and the control unit 12 for controlling the automatic culture apparatus.

As illustrated in a perspective view of FIG. 7A and a top view and a side view of FIG. 7B, the plurality of culture vessels 201 for culturing cells, the heat storage portions 701 for covering the culture vessels, respectively, and the culture vessel base 202 on which the culture vessels 201 and the heat storage portions 701 are arranged are provided in the incubator (not illustrated). The plurality of culture vessels 201 are placed in a circular shape as illustrated in FIG. 7B, and each of the heat storage portions 701 has a trapezoidal shape as illustrated in FIG. 7B.

The culture vessel base 202 has a groove-shaped guide (not illustrated) to determine positions of the culture vessels 201 and the heat storage portions 701. Cells in the culture vessels 201 are observed with the use of the microscope 400. Further, the flow channel portion 2 including a drive system such as the electromagnetic valves 212 and the tube pumps 213 for feeding a medium or the like to the culture vessels 201 is arranged. The automatic culture apparatus implements, for example, cell seeding by feeding a cell suspension to the culture vessels 201, culture in which a temperature is maintained at 37° C. while gas is appropriately exchanged, exchange of media by which an old medium is discharged and a new medium is supplied, and observation of the cells with the microscope. Note that, although steps implemented by the automatic culture apparatus in this example are cell seeding, exchange of media, culture, and observation with the microscope, it is needless to say that some steps may be manually performed.

As described above, the culture vessel 201 is surrounded by the heat storage material 605 in the automatic culture apparatus, and the heat storage material 605 is heated together with the culture vessel in the automatic culture apparatus. At this stage, the heat storage portion 701 is not covered with the heat insulation material, and therefore heat is efficiently supplied from the incubator. Therefore, there is no need to provide means such as a heater for heating the heat storage portion 701. With this, there is no change in the structure of the automatic culture apparatus. Further, in this state, there is no optical problem with observation with the microscope.

On, for example, the day before transplantation, one or a plurality of culture vessels 201 are taken out for shipping examination to determine whether or not transplantation is implementable. The number of culture vessels to be removed is arbitrary as one embodiment, and a user can determine the number of culture vessels on the basis of, for example, observation results of the cells. After the culture vessel 201 to be removed is determined, the door 402 of the incubator 401 illustrated in (A) on the left side of FIG. 4 is opened, and then the flow channel tubes 302 attached to the culture vessel 201 are sterilely cut. After cutting, the culture vessel 201 and the heat storage portion 701 are taken out. Alternatively, this operation may be implemented through the small window 409 provided on the side surface of the incubator 401 instead of the door 402. In this case, it is possible to further reduce decrease in a temperature in the incubator 401.

The culture vessel 201 and the heat storage portion 701 are quickly put in the heat insulation portion 601 and are then taken out from the automatic culture apparatus. Then, the door or the small window 409 of the incubator 401 is closed. The temperature in the incubator is, for example, 37° C., whereas a room in which the incubator is arranged has, for example, 25° C., and thus the temperature in the room is generally lower than that in the incubator. Therefore, the inside of the incubator is exposed to air outside the incubator having a temperature which is lower than that in the incubator, and the temperature thereinside is decreased while the door of the incubator is open. However, because the culture vessel 201 is surrounded by warming means, it is possible to prevent decrease in the temperature. The removed culture vessel is delivered while being surrounded by the heat insulation portion. Therefore, it is possible to maintain a temperature until the shipping examination is performed. That is, it is possible to implement the shipping examination under the same condition as the condition which has been set at the time of production. Note that, in the case where a culture vessel to be taken out for examination on the day before transplantation is not arbitrarily selected during culture but is determined in advance, culture vessels can be provided so that only the culture vessel for examination is removable and a plurality of remaining culture vessels for transplantation are connected. In this case, at least two integrated culture vessels are collectively treated in steps such as a transportation step. That is, the culture vessels other than the culture vessel for examination to be taken out and the heat storage portions containing the culture vessels can be integrally provided and can be integrally taken out from the incubator.

In the above description, in the case where the culture vessel 201 and the heat storage portion 701 are covered with the heat insulation portion 601, a necessary heat insulation portion and a necessary heat insulation member are supplied to the incubator 401 and are heated to have 37° C. in advance, and therefore it is possible to cover the culture vessel 201 and the heat storage portion 701 with the heat insulation portion 601 in the incubator 401 while further preventing decrease in a temperature.

As described above, when a culture vessel is taken out on the day before transplantation, after the culture vessel to be used for the shipping examination is taken out from the incubator or immediately before the culture vessel is taken out, the culture vessel and the heat storage portion are quickly put in the heat insulation portion and are delivered to the safety cabinet or the like in that state. Meanwhile, culture vessels which are not used for the shipping examination are held in the incubator as they are. At this time, as illustrated in FIG. 7A, because the culture vessel is surrounded by the heat storage portion 701, it is possible to prevent decrease in a temperature of the remaining culture vessels 201 even in the case where the inside of the automatic culture apparatus is exposed to open air. Further, in the case where the culture vessels are taken out on the day of transplantation, the culture vessels to be used for transplantation are sequentially taken out from the incubator. The culture vessels are quickly received into the heat insulation portion and are then delivered to the safety cabinet or the like in the same way as the culture vessel taken out on the day before transplantation.

On the day before transplantation or on the day of transplantation, the culture vessel taken out from the apparatus is delivered in a state of being received by the heat storage portion 701 and the heat insulation portion 601 as illustrated in FIG. 6C. With this, decrease in a temperature is prevented even in the case where the culture vessel is exposed to a room temperature which is lower than the temperature in the culture space.

In the case where the culture vessel is moved to a room having different cleanliness, the culture vessel is passed through a pass box in the CPC, and, at that time, ethanol for disinfection or the like is sprayed in some cases in order to prevent cross-contamination. The sprayed ethanol for disinfection decreases a temperature while being vaporized. However, such decrease in a temperature can be prevented also by the heat insulation material. The heat insulation material has resistance to ethanol for disinfection or the like.

A biological sample is processed in the safety cabinet as necessary. An example of processing is as follows. In the case of a culture vessel for shipping examination taken out on the day before transplantation, the culture vessel is examined in the safety cabinet. Whether or not the biological sample can be collected, expression of specific protein, a cell survival rate, and the like are evaluated. Depending on the purpose, examination may be non-invasively implemented, then the biological sample may be put in the automatic culture apparatus again, and a culture schedule and the like may be changed by the control mechanism in accordance with examination results, and thus the culture step may be modified to be more effective. In that case, in order to continue culture even after the examination, the flow channel tubes are sterilely connected again in the case of the closed-system culture vessel. In the case of the open-system culture vessel, the biological sample is sterilely returned to the automatic culture apparatus as it is.

In the case of the culture vessel for transplantation taken out on the day of transplantation, and, in particular, in the case of long-distance transportation, a medium is exchanged for a medium for transportation as necessary. That is, the cover of the culture vessel is opened, a medium used for culture is removed and a medium for transportation is put in, and the cover is closed again. A cover having a shape suitable for transportation may be used as the cover of the culture vessel. In such processing in the safety cabinet, the culture vessel is warmed by a hot plate as necessary in order to prevent decrease in a temperature.

At this time, as illustrated in FIG. 6D and FIG. 8, the culture vessel is placed on the hot plate in a state in which only the lower surface of the heat insulation portion 601 is removed. Because the hot plate 801 and the heat storage portion 701 are directly in contact with each other, heat is efficiently conducted to the heat storage portion 701. Meanwhile, because surfaces other than the lower surface are covered with the heat insulation portion 601, emission efficiency of heat is reduced even in the case where the culture vessel is exposed to open air having a temperature which is lower than that in the heat storage portion 701.

After necessary processing is implemented in the safety cabinet and the culture vessel is passed through the pass box, the culture vessel is received into the transportation vessel in a shipping room in the CPC. The transportation vessel is selected depending on the transportation time. A case where the transportation time is short will be described. Specifically, there is assumed a case where the CPC and the operating room are placed in the same site and the culture vessel is delivered by hand in a location where the temperature is not greatly changed.

Figure 9A:
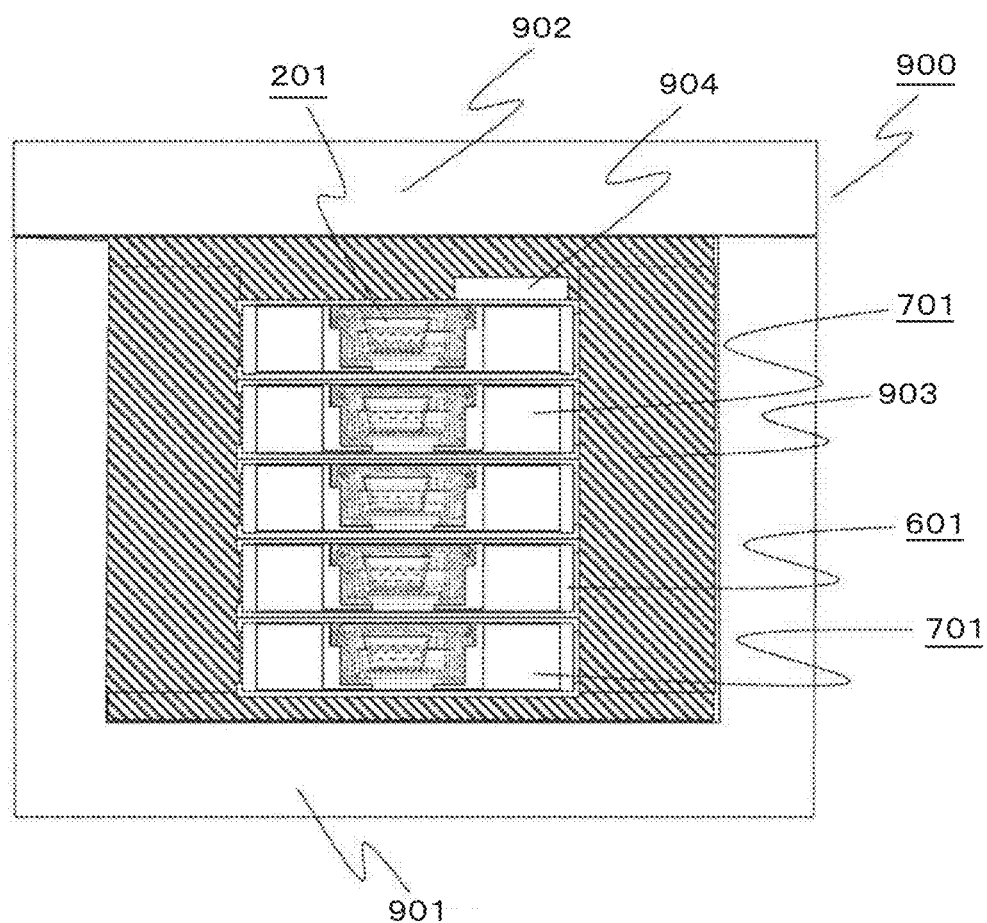
FIG. 9A illustrates a state in which culture vessels are received in a holding vessel according to Example 1.

FIG. 9A illustrates a case where the culture vessels are taken out from the automatic culture apparatus and are transported as they are. An outermost shell of a transportation vessel 900 is a containing vessel main body portion 901 and a containing vessel cover portion 902, and a heat insulation member 903 is provided therein. An environment sensor 904 for measuring a temperature and the like during transportation is provided. The culture vessels 201 are contained in a state of being surrounded by the heat storage portion 701 and the heat insulation portion 601. Therefore, emission of heat is prevented in two ways by the heat storage portions 701 and the heat insulation portions 601 covering the heat storage portions 701.

Figure 9B:
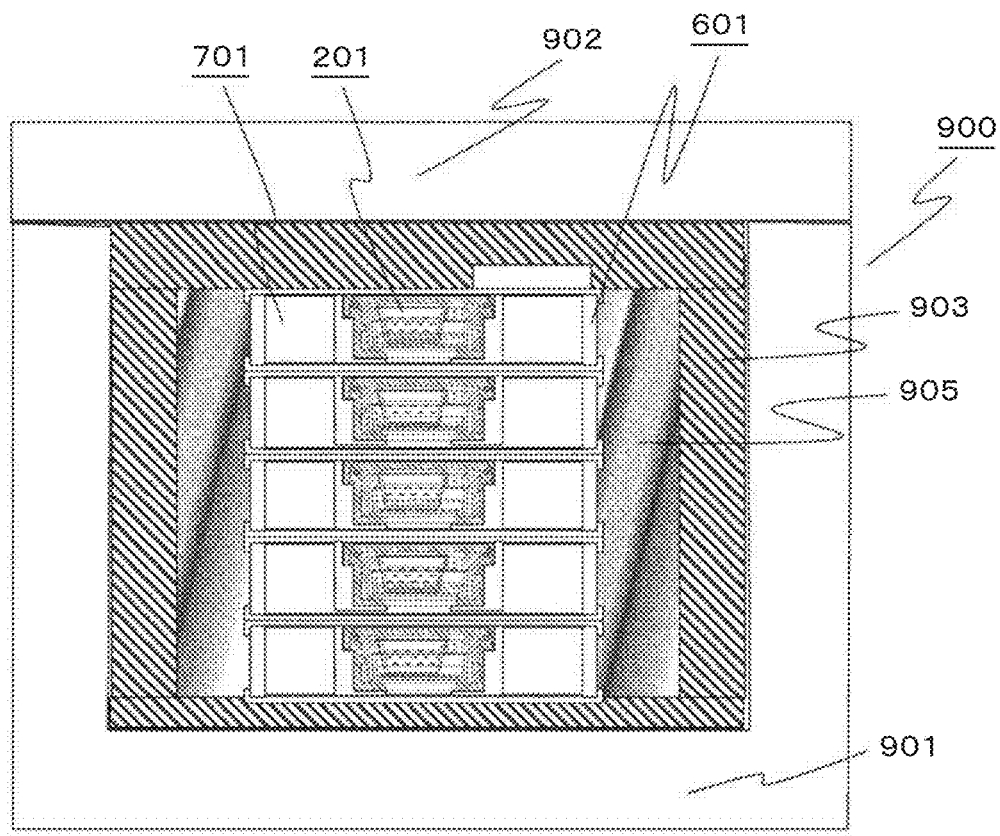
FIG. 9B illustrates another example where culture vessels are received in a holding vessel according to Example 1.

FIG. 9B illustrates a state in which a heat storage material 905 of the transportation vessel 900 is covered with the heat insulation member 903. Because the heat storage material is covered with the heat insulation member, the heat insulation member does not warm the culture vessel 201 but compensates heat gradually emitted to outside of the transportation vessel. As a result, a temperature maintaining time of the culture vessels 201 becomes longer.

Figure 9C:
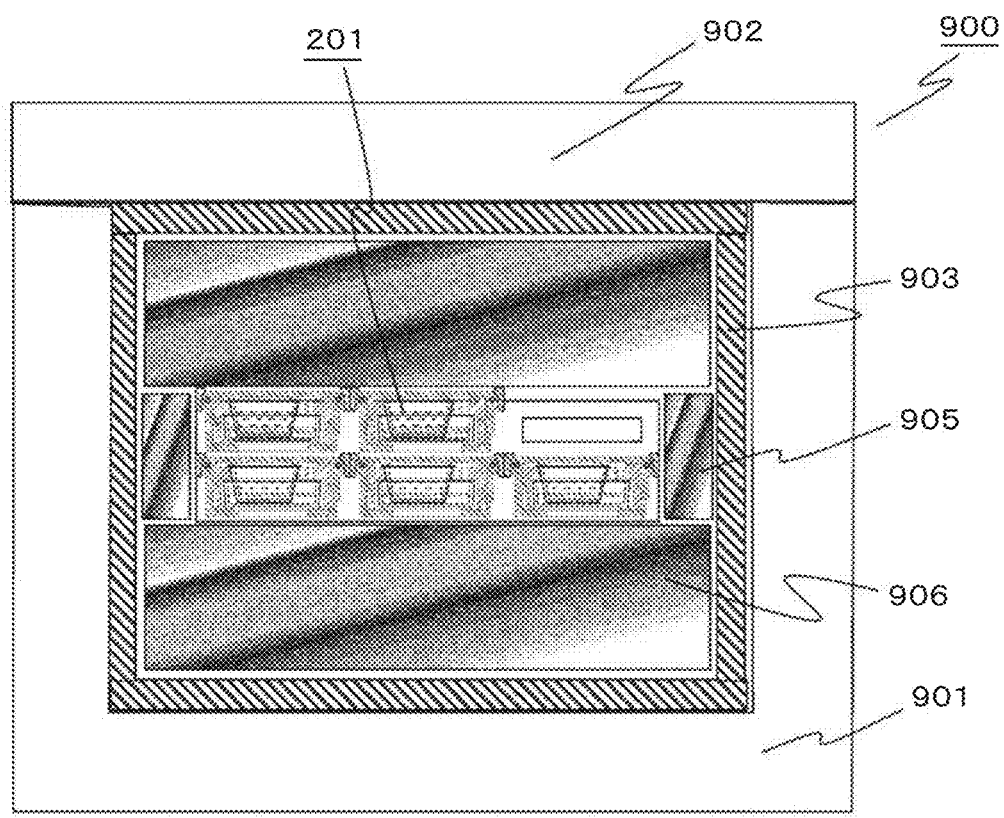
FIG. 9C illustrates another example where culture vessels are received in a holding vessel according to Example 1.

A case where the transportation time for transporting the culture vessels to the operating room for treatment is long is illustrated in FIG. 9C. Long-distance transportation is assumed to be a case where, for example, the CPC which is a production location and the operating room which is a treatment location are not placed in the same site and the culture vessels need to be transported by means such as an airplane and a vehicle. FIG. 9C illustrates a case where a heat storage material 408 is added in the transportation vessel, as compared with the case of FIG. 9B. Because the heat storage material 408 warms the culture vessels, the culture vessels are contained in a state in which the heat insulation portions covering the heat storage portions are removed. In the case of long-distance transportation, the temperature maintaining time needs to be satisfactorily long. Therefore, a heat storage material is taken out from a thermostat immediately before long-distance transportation and is used for transportation. A heat storage material having a large heating storage capacity is preferably used. For example, a pure substance $C_{20}H_{42}$ of hydrocarbon has a melting point of 36.4° C., which is close to the culture temperature of 37° C., and therefore, by heating the pure substance to 37° C. in advance and then using the heated pure substance, it is possible to maintain a temperature for long time while a state is changed from a fluid to a solid.

Figure 10A:
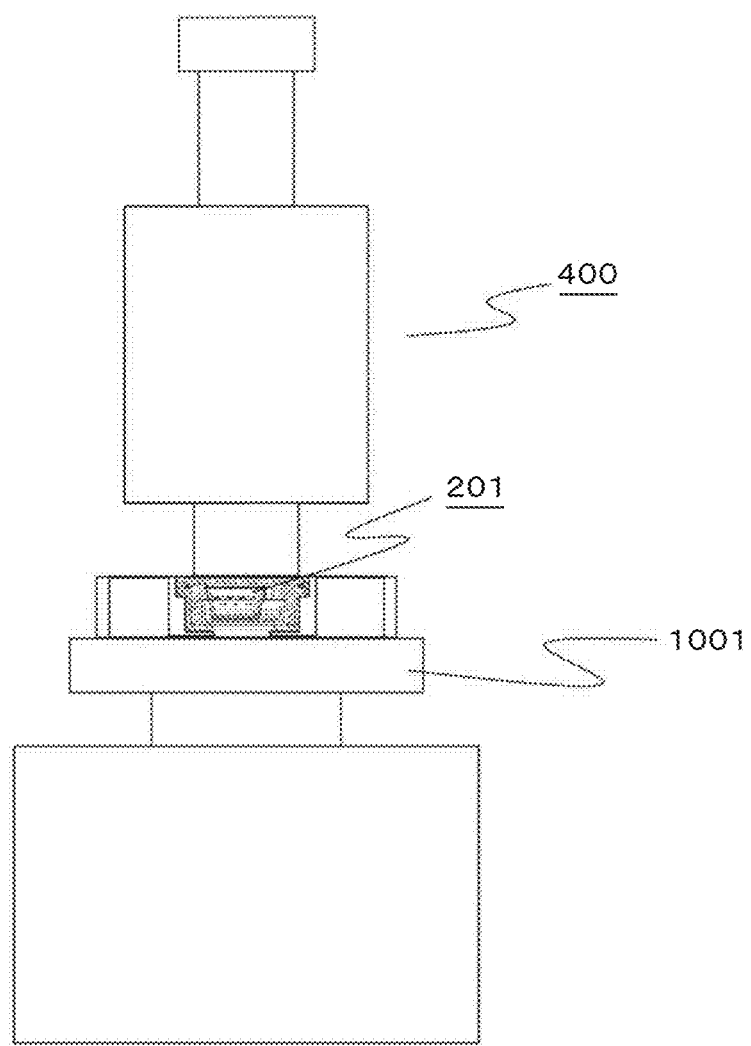
FIG. 10A illustrates observation of a culture vessel provided with a heat storage material with a microscope according to Example 1.
Figure 10B:
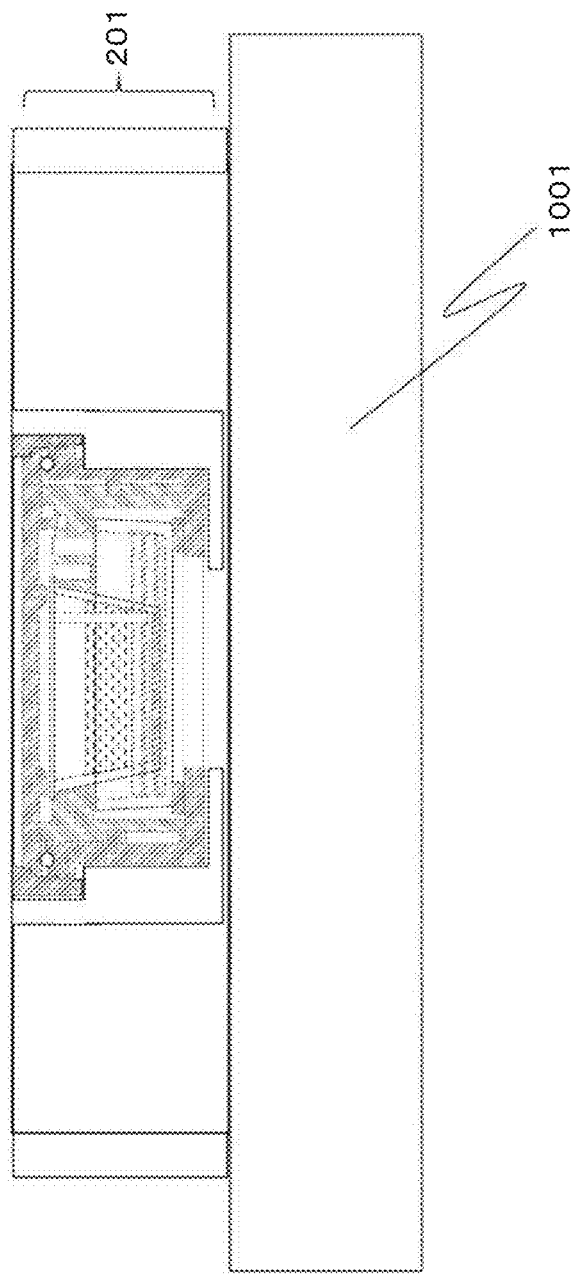
FIG. 10B illustrates observation of a culture vessel provided with a heat storage material with a microscope according to Example 1.

As illustrated in FIG. 10A and FIG. 10B, a state of cells is checked after, for example, transportation as necessary by observation with the microscope which is a non-invasive method. For example, after the transportation step, whether or not quality of the cells has been changed is evaluated. At the time of observation, it is necessary to place the culture vessel 201 on a stage 1001 of the microscope 400. Further, the culture vessel 201 needs to be optically transparent. It is also necessary to focus on the cells. That is, it is necessary to have a satisfactorily small distance between an objective lens and the cells. In view of those points, as illustrated in FIG. 6E, at the time of observation, the upper and lower surfaces 609 and 610 of the heat insulation portion 601 are removed so that the culture vessel is optically transparent. Further, in order to reduce the distance between the objective lens and the cells, the upper and lower surfaces are arranged to cover the side surface 611 as illustrated in FIG. 6C and the height of the side surface 611 is set to be the same as that of the culture vessel after the upper and lower surfaces are removed. In other words, by removing the upper and lower surfaces, the heat insulation portion 601 is closer to the stage in a vertical direction.

Immediately before transplantation, the culture vessels covered with the heat insulation portion 601 and the heat storage material are taken out from the transportation vessel which has been carried to the operating room. After the culture vessels are taken out, the covers of the culture vessels are sterilely opened, and biological samples are taken out and are used for treatment of a patient. Note that, in the case where a temperature-responsive culture surface is used in each culture vessel, the culture vessel is taken out from the heat storage portion and the heat insulation portion, is then moved into a thermostat having, for example, 20° C., and is subjected to chilling treatment for allowing the culture vessel to stand for, for example, about 30 minutes. The hydrophobic temperature-responsive culture surface is changed to the hydrophilic one, and therefore a form of cells adhered onto the temperature-responsive culture surface spontaneously changes and the cells spontaneously peel off.

Figure 11A:
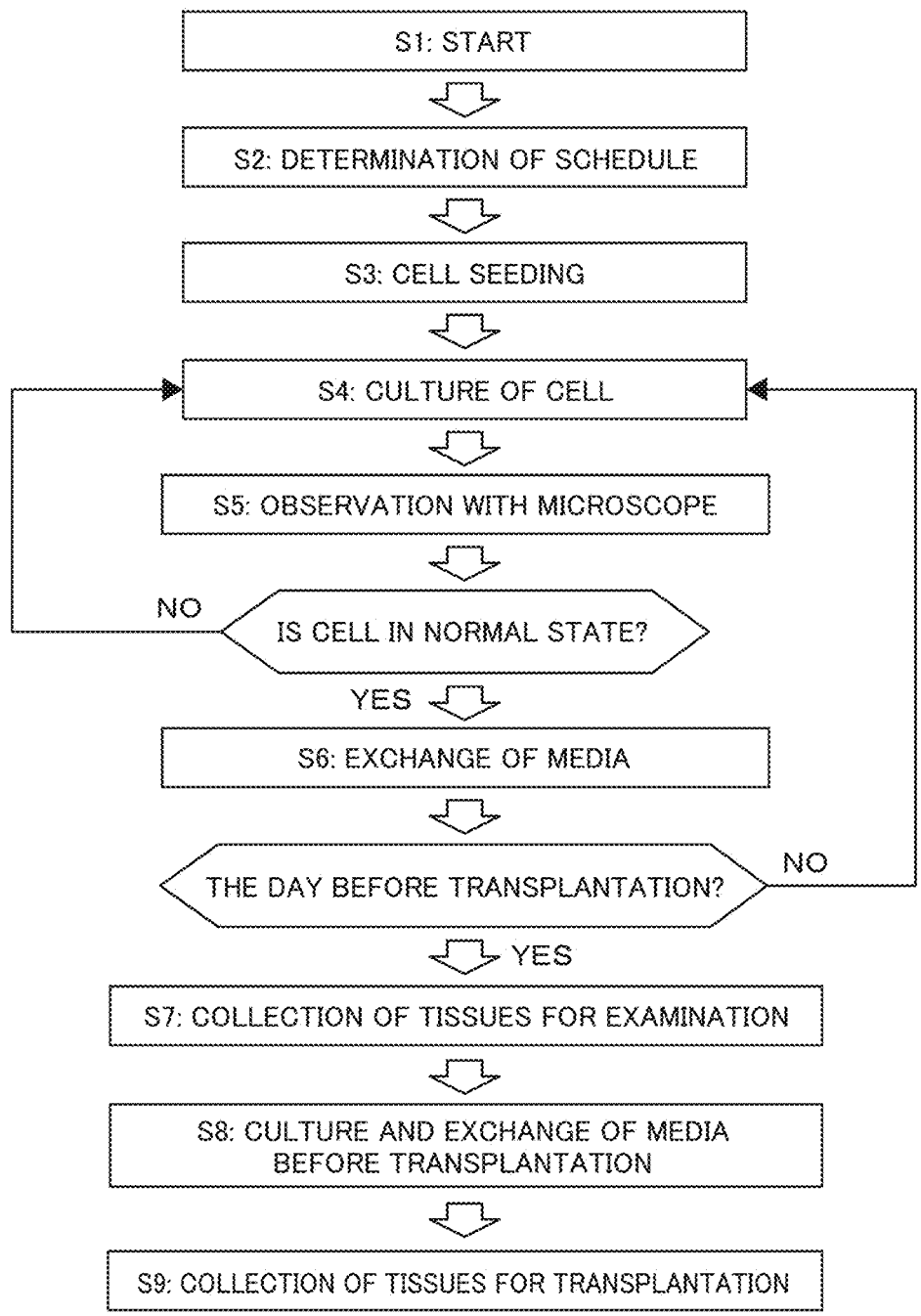
FIG. 11 is a flowchart of a culture protocol of a culture apparatus according to Example 1.
Figure 11B:
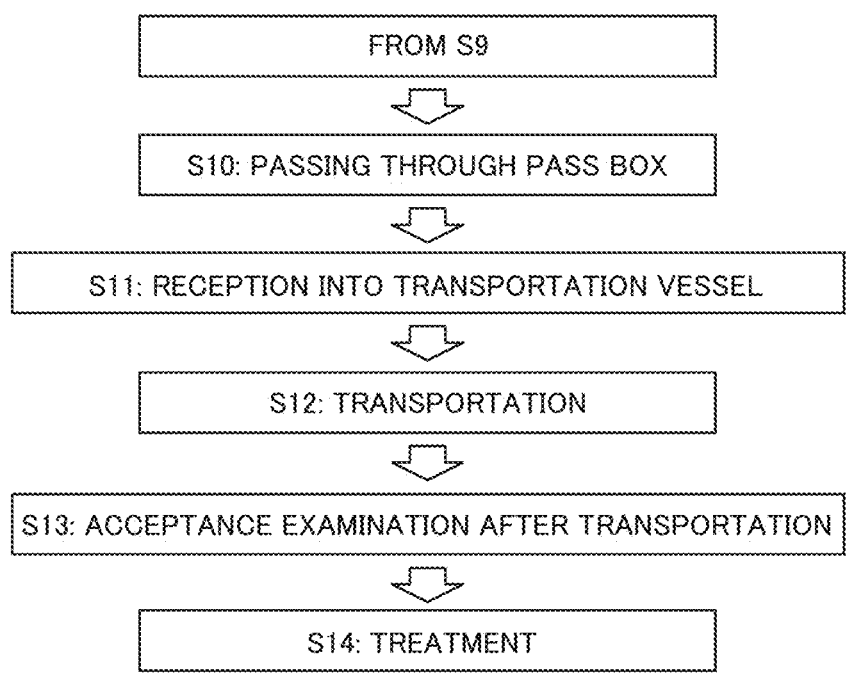

A series of steps of producing and transporting biological samples with the use of culture vessels provided with a heat storage material, the culture vessels having the structure of the example described above, will be described with reference to a flowchart of FIG. 11. In order to perform the following steps, culture vessels are arranged in the automatic culture apparatus in advance. As illustrated in FIGS. 1 and 2, the flow channel includes the culture vessels, the cell bottle containing a cell suspension, the medium bottle containing a medium, the waste fluid bag for collecting waste fluid, and the flow channel tubes connecting them. The culture vessels 201 are sequentially put in the heat storage portions 701 arranged in advance on the culture vessel base 202. After the flow channel is arranged, normality of arrangement is checked, and then the processing proceeds to Step S1.

<Step S1: Start>

The automatic culture apparatus is started. An operator starts the automatic culture apparatus by pushing a start switch of an operation unit in the control unit 12. Note that the inside of the apparatus is a clean environment because the inside thereof has been sterilized or disinfected in advance. A value related to an internal environment of the automatic culture apparatus is displayed on an operation screen of a display of the control unit 12. On the operation screen of the display of the control unit, it is confirmed that the internal environment of the automatic culture apparatus is appropriate. For example, it is confirmed that a temperature of the incubator 401 is 37° C. Those numerical values are not limited thereto and can be selected from, for example, a range of temperatures from 0° C. to 45° C.

<Step S2: Determination of Schedule>

An automatic culture schedule to be implemented by the automatic culture apparatus is determined. The automatic culture schedule to be implemented by the automatic culture apparatus is inputted in accordance with the kind and amount of cells to be cultured. Conditions, such as date, frequency, and a fluid volume, for operation such as cell seeding, exchange of media, observation with a microscope, collection of waste fluid, collection of tissues for examination, and collection of tissues for transplantation are inputted via the control terminal 13 or the like connected to the control unit 12.

<Step S3: Cell Seeding>

After the electromagnetic valves 212 are appropriately opened and closed, the tube pumps 211 are operated to absorb the cell suspensions from the cell bottles. In an example of regeneration of an esophagus, in order to culture oral mucosal epithelium cells, the cell suspensions are oral mucosal epithelium cells suspended in a KCM medium (keratinocyte culture medium) and feeder cells such as 3T3-J2 cells or NIH-3T3 cells also suspended in a KCM medium. Those two kinds of cells are contained in different cell bottles, respectively.

At the time of cell seeding, the cell suspensions are fed to the culture vessels 201 from the two cell bottles 4. The electromagnetic valves connected to the culture vessels 201 to which fluids are to be fed and the flow channel are opened in advance so as to feed the fluids. Meanwhile, the electromagnetic valves connected to the culture vessels to which the fluids are not to be fed and the flow channel are closed so as not to feed the fluids. Cell seeding is sequentially implemented with respect to the upper layers and the lower layers of the ten culture vessels.

As described above, the epithelial cells are passed through the flow channel circuit (1) indicated by the solid lines in FIG. 2 and are sequentially seeded in the upper layers of the respective culture vessels 201. The feeder cells are passed through the flow channel circuit (2) indicated by the broken lines and are sequentially seeded in the lower layers of the respective culture vessels. Note that, immediately before the fluids are fed, the cell suspensions are absorbed and discharged so that cell distribution in the cell bottles is uniform and cell density of the cell suspensions to be fed is uniform. After the cell suspensions are seeded in all the culture vessels, the actuator provided in a lower part of the culture vessel base 202 on which the culture vessels are arranged is operated. The culture vessels are held in a horizontal state during cell seeding and during cell culture, and the culture vessels 201 are inclined by the actuator 203 immediately after cell seeding and during exchange of media. During cell seeding, the culture vessels are continuously shaken to have uniform cell distribution. Thereafter, the culture vessels are returned to be in the horizontal state and culture is performed in that state.

<Step S4: Culture of Cells>

Culture is performed in the culture vessels 201 for a predetermined time while the culture vessels 201 stand horizontally. In an example of oral mucosal epithelium cells, a standing time period is set to about 3 days after seeding. The inside thereof is maintained at 37° C. by the incubator during culture. Air in the apparatus is always stirred by a fan so that temperature distribution is always uniform. Note that, although not described in this example, it is possible to improve safety of production by attaching a particle counter and a viable cell counting device to the apparatus so as to monitor cleanliness.

During culture and immediately after cell seeding, exchange of gas for feeding gas containing predetermined components into the culture vessels is performed. The exchange of gas is implemented about several times a day during culture. In the case of culturing oral mucosal epithelium cells, air containing $CO_2$ concentration of 5% is supplied into the culture vessels. The gas is supplied from the gas supply unit and, before being fed to each culture vessel, the gas is passed through the humidification bottle portion 11 to be saturated with water molecules. This prevents a situation in which moisture is evaporated from the medium in each culture vessel and medium components are changed as a result. Further, the gas is directly fed to each culture vessel by using a gas pressure not via the tube pump but via the air-supply circuit provided in parallel with the tube pump. With this, the air supply rate can be improved, as compared with a case where the gas is fed via the tube pump, which results in improvement of the gas exchange efficiency. Further, a load to the tube pump is eliminated. Waste gas which has been supplied to the culture vessels is discharged to outside of the flow channel through a filter. Further, an air pressure in the flow channel is adjusted through the filter as necessary. As the filter, there is used a filter having such quality that does not allow, for example, particles having 0.22 μm or more to pass therethrough.

In the culture vessels 201 to be used for the apparatus of this example, a flow channel tube used for feeding fluid and a flow channel tube used for supplying air are not separated. That is, the flow channel tube used for feeding fluid also has a function of supplying air. With this structure, the number of flow channel tubes to be connected to the culture vessels 201 is reduced, as compared with a case where a flow channel tube used for feeding fluid and a flow channel tube used for supplying air are independently provided. This results in simplification of the flow channel.

<Step S5: Observation with Microscope>

A cell image is obtained with the use of the microscope 400 arranged in the observation portion 8 in the automatic culture apparatus. A light source arranged in the automatic culture apparatus appropriately emits light, and the microscope 400 focuses on cells and captures an image thereof. The image is captured by arbitrarily defining a fixed point on a culture surface as necessary. The obtained cell image is stored in a database and is seen on the control terminal arranged outside the apparatus. Frequency and a timing of exchange of media are adjusted on the basis of determination based on information on a growth state of cells, the information being obtained by observation with the microscope. In the case where, for example, cells are not satisfactorily adhered, exchange of media in S6 is not implemented and culture of cells in S4 is continued.

Unless a cell image is automatically captured, a user appropriately operates the microscope 400 by manual operation to observe the cells and capture an image of the cells. The captured image, as well as the cell image that has been automatically captured, can be stored.

<Step S6: Exchange of Media>

Exchange of media is implemented every several days during culture. A medium kept at 4° C. in the refrigerator is fed to the preheating bottle and are preheated. The medium is heated by thermal conductivity caused by bringing the preheating bottle into contact with the receiving portion provided around the preheating bottle and by a gas phase having 37° C. by the incubator. For example, preheating is performed for several hours to one day, thereby increasing a temperature to 36° C. or more. Then, the medium is used for exchange of media.

Then, an old medium is discharged from the culture vessels 201. The culture vessels are inclined on a discharge port side by the actuator so that the old medium is completely discharged. After discharging the old medium, a preheated new medium is quickly supplied into the culture vessels. This prevents drying of cells on the culture surfaces and decrease in a temperature. The old medium is finally discharged into the waste fluid bag portion 7 as illustrated in FIG. 1. The medium is assumed to be used for medium component analysis, and therefore the medium in the upper layers of the culture vessels 201 and the medium in the lower layers thereof are separately collected in this example.

Note that, in cell seeding and exchange of media described above, the flow channel circuit illustrated in FIG. 2 causes the cell suspensions and the medium to flow in one direction. In other words, the old medium which has been used for culture in the culture vessels and the new medium which has not been used for culture yet are not mixed. The old medium and the new medium are different in, for example, an amount of glucose consumed by cells and an amount of lactic acid produced by the cells, and therefore, in the case where both the media are mixed when the media are exchanged, a cultural environment is changed. By preventing mixing of both the media with this structure of the apparatus of this example, it is possible to improve reproducibility of cell culture. Further, in the case where the discharged old medium is subjected to medium component analysis, it is also possible to improve accuracy of the medium component analysis by preventing mixing of the new medium with the old medium.

<Step S7: Collection of Tissues for Examination>

One or a plurality of culture vessels 201 are collected for examination during culture on, for example, the day before a scheduled date of transplantation. The door of the automatic culture apparatus is opened, and the flow channel tubes 302 of the culture vessels 201 for examination are sterilely cut by means such as heat-welding. Thereafter, the culture vessels 201 are taken out together with the heat storage portions 701 and are put in the heat insulation portions 601 prepared in advance. Note that, as described above, the heat insulation portions 601 may be put in the incubator 401 at the time of start of culture to be preheated. With this, decrease in a temperature becomes further slower. The removed culture vessels 201 are delivered to the safety cabinet or outside of the CPC and are examined quickly. For example, the number of cells in a biological sample, a survival rate, expression of specific protein, and the like are evaluated. After the culture vessels for examination are taken out, the door of the incubator is quickly closed.

The inside of the incubator 401 is exposed to a room temperature and a temperature is decreased while the above operation is performed. However, in the case of the structure of this example, as illustrated in FIG. 7A and FIG. 7B, culture vessels, which are not for examination but for transplantation, are also surrounded by the heat storage portions 701 heated to have 37° C. in advance. Therefore, even in the case where the inside of the incubator 401 is exposed to air having a room temperature when the door of the incubator 401 is opened, it is possible to prevent decrease in the temperature. With this, in particular, cells which have not been transplanted yet are prevented from peeling off from the temperature-responsive culture surfaces having the phase transition temperature of 32° C. in the culture vessels 201. After the operation is completed, an air conditioner and a heater are controlled to adjust the temperature so that the temperature is promptly returned to be, for example, 37° C. which is a culture temperature. This also recovers a heating storage amount of the heat storage portions 701 which have emitted heat in this process, the heat storage portions 701 surrounding the culture vessels 201 other than the culture vessels 201 for examination.

The sterilized detachable portion 303 is, for example, a heat-weldable flow channel tube, and two parts having a cutting portion in between are heat-welded and then the part therebetween is cut. With this, even after the culture vessel is removed, it is possible to maintain sterility in the removed culture vessel, the culture vessels which have not been removed, and the flow channel. The culture vessel which has been taken out is examined quickly thereafter to determine whether or not transplantation is implementable. Further, examination results are analyzed and a culture state at that point is evaluated, and, based on evaluation results of the culture state, a culture schedule of the culture vessels in which culture is continued in the culture space can be changed to an appropriate culture schedule.

<Step S8: Culture and Exchange of Media Immediately Before Transplantation>

Culture of cells and exchange of media are implemented in the same way as Steps S4 and S6.

<Step S9: Collection of Tissues for Transplantation>

In the case where it is detected that transplantation is implementable on the basis of the examination results in Step S7, the display of the control unit shows that culture has been completed. Thereafter, the culture vessels are sterilely removed from the flow channel together with the heat storage portions, are put in the heat insulation portions, and are taken out from the incubator in the same way as Step S7. The culture vessels are carried into the safety cabinet and are processed as necessary.

In order to prevent decrease in a temperature of the culture vessels in the safety cabinet, a heat block or a hot plate which is set to have the same temperature as that in the incubator is used as necessary. Immediately before the culture vessels provided with a heat storage material are placed on the heat block or the like, the lower surfaces of the heat insulation portions 601 are removed and then the culture vessels are placed on the heat block. The lower surfaces of the heat storage portions 701 are heated by the heat block, emission of heat from the surfaces other than the lower surfaces is prevented by the heat insulation portions 601. The covers of the culture vessels which have been moved into the safety cabinet are removed and the medium in the culture vessels is exchanged for a medium for transportation as necessary.

<Step S10: Passing Through Pass Box>

In the case of delivery to the shipping room from a cell preparation room for culturing cells, the culture vessels are passed through the pass box. In the case were the culture vessels are passed through the pass box, ethanol for disinfection or the like is sprayed to disinfect the outside thereof as necessary. Although evaporation of the sprayed ethanol for disinfection may decrease a temperature, such decrease in a temperature is prevented by the heat insulation portions.

<Step S11: Reception into Transportation Vessel>

The culture vessels provided with a heat storage material are put in a short-distance or long-distance transportation vessel in the shipping room. As described above, the transportation vessel is a vessel covered with a heat insulation material, and this prevents decrease in a temperature in the transportation step. Further, a monitoring device is provided therein. The monitoring device is turned on before being provided therein and starts measuring. The monitoring device measures a temperature, pressure, shock, and the like during the whole transportation process.

<Step S12: Transportation>

The transportation vessel is carried to outside of the CPC.

<Step S13: Acceptance Examination after Transportation>

Before treatment in the operating room, cells are observed with the use of a microscope as necessary as acceptance examination. In the case where observation with the microscope is implemented, the culture vessels covered with the heat insulation portion and the heat storage portions are taken out from the transportation vessel. The culture vessel is placed on a stage of the microscope in a state in which the upper and lower surfaces of the heat insulation portion are removed, and cells are observed. With this, the cells can be observed while decrease in a temperature is reduced. In the case where it is confirmed that the transported culture vessel is suitable for treatment as a result of evaluation, preparation of the treatment is started. The culture vessels are contained in the transportation vessel to maintain a temperature until the treatment is started.

<Step S14: Treatment>

In the case where preparation of the treatment is made, the transportation vessel is moved to the operating room. When the transportation vessel arrives at the operating room, the culture vessels are taken out together with the heat insulation portions and the heat storage portions. Then, the culture vessels are taken out from the heat storage portions. Subsequently, biological samples are taken out from the culture vessels. In the case where temperature-responsive culture surfaces are used as the culture vessels, there is performed chilling treatment which allows the culture vessels to stand for 30 minutes in a thermostat having, for example, 20° C. in advance.

EXAMPLE 2

As Example 2, there will be described an example of a culture vessel provided with a heat storage material including a heat storage portion which has a different structure from any of the structures of the heat storage portions illustrated in FIG. 6A to FIG. 6F. The heat storage portion conducts heat stored in advance to the culture vessel to maintain a temperature of the culture vessel. Meanwhile, because the heat storage portion is cooled by outside air, a temperature on an outer circumference side becomes lower than that in the inside as time passes. A quantity of heat enclosed in the inside is efficiently transmitted to the culture vessel, and therefore heat is efficiently transmitted to the culture vessel from the inside of the heat storage portion in this example.

Figure 12A:
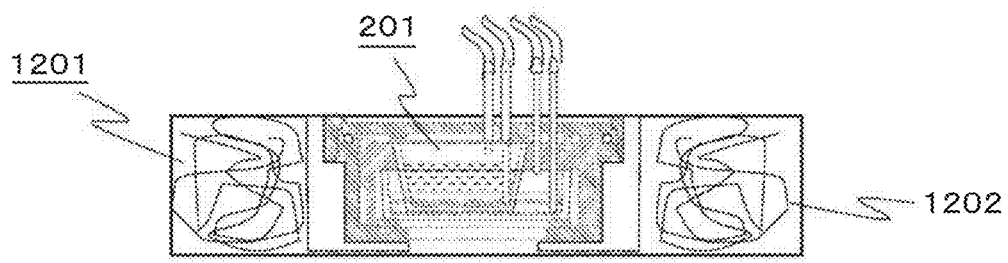
FIG. 12 illustrates structures of a culture vessel provided with a heat storage material according to Example 2.
Figure 12B:
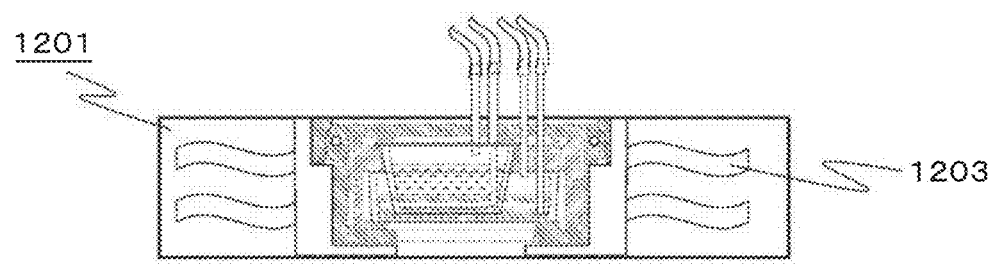
Figure 12C:
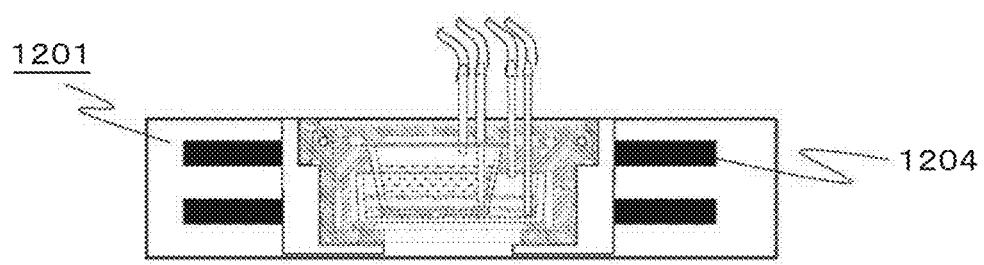
Figure 13C:
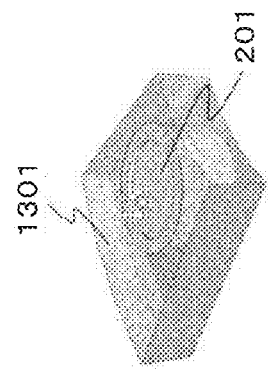
FIG. 13 illustrates culture vessels provided with a heat storage material on a culture vessel base according to Example 3.
Figure 13D:
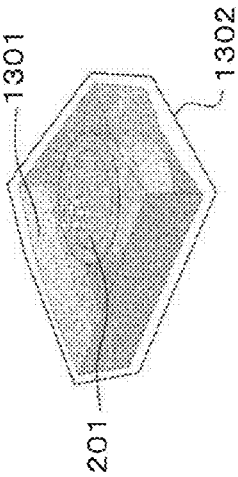
Figure 13A:
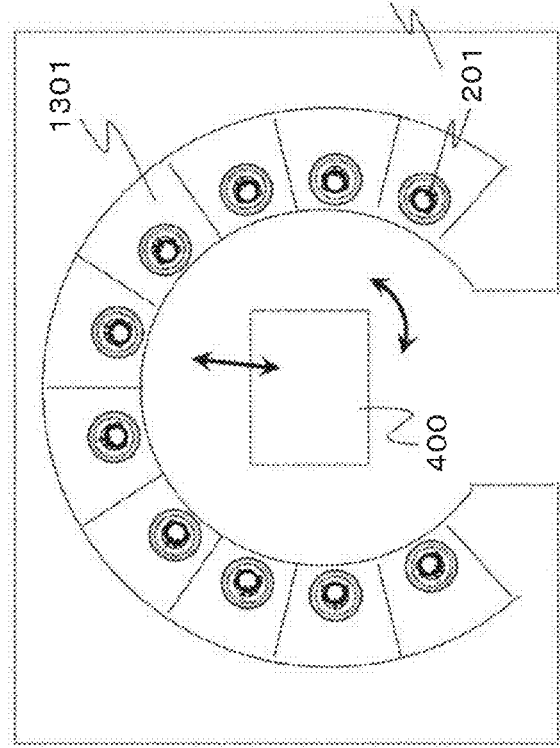
Figure 13B:
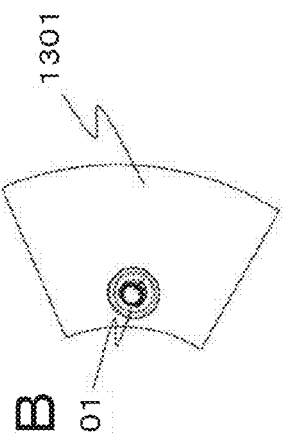

As illustrated in FIG. 12A to FIG. 12C, a thermal conductor such as a linear metal 1201, a planar metal 1202, or a bar metal 1203 is arranged from the inside of the heat storage portion to the culture vessel. Note that a volume of the inside of the heat storage portion is reduced as a volume of the above internal metal is increased. As a result, the temperature maintaining time is reduced. In the case of the structure of this example, a shape and arrangement of the thermal conductor are selected in accordance with a necessary temperature maintaining time.

EXAMPLE 3

An example where an arrangement position of a culture vessel in a heat storage portion is changed will be described as Example 3. The heat storage portion of the culture vessel provided with a heat storage material is provided for maintaining a temperature of the culture vessel, and therefore it is desirable that spatial distribution of the heat storage portion covering the culture vessel be uniform. In other words, it is the most preferable that the culture vessel be positioned at the center of the heat storage portion as in the structure of Example 1 described above.

Meanwhile, as illustrated in FIG. 1 and FIG. 7B, in the case where the culture vessel arranged in the automatic culture apparatus is observed with the use of the microscope 400 of the observation portion 8, the microscope 400 needs to be moved to be closer to the culture vessel. In this case, a moving mechanism of the microscope 400 becomes large as a moving distance is increased, and, as a result, the automatic culture apparatus becomes large. This causes increase in costs and therefore is not preferable.

(A) of FIG. 13 illustrates a state in which a plurality of culture vessels provided with a heat storage material, in each of which a side of each heat storage portion 1301, the side being close to the microscope 400, is thin so that the moving distance in which the microscope approaches is reduced, are arranged on the culture vessel base 202. The microscope 400 is positioned at the center of the culture vessel base 202, and therefore center sides of the trapezoidal heat storage portions 1301 surrounding the culture vessels 201 are thin. As in (B) of FIG. 13 which illustrates a single culture vessel provided with a heat storage material, which is taken out for examination, the culture vessel 201 is eccentrically positioned in a trapezoidal heat storage portion 1301, i.e., is positioned on one side of a pair of facing side surfaces. With this, the culture vessel is closer to the microscope 400 of the observation portion, and therefore it is possible to reduce the moving distance. This makes it possible to reduce the size of the apparatus and an observation time. (C) of FIG. 13 is a perspective view of a culture vessel provided with a heat storage material providing a trapezoidal heat storage portion having an eccentric structure of this example, and (D) of FIG. 13 illustrates a perspective view of a heat insulation portion and a culture vessel provided with the heat storage portion.

FIG. 14 illustrates two sets of rectangular culture vessel bases 1402 in each of which rectangular heat storage portions 1401 are arranged in a straight line. The observation portion 8 in which the microscope 400 is arranged moves back and forth and moves from side to side (X and Y directions). Aside of each rectangular heat storage portion 1401 of this example, the side being closer to the microscope 400, i.e., the side being a space side between two culture vessels 201, is also thin. That is, the culture vessel 201 in each heat storage portion 1401 is eccentric on the microscope 400 side in the observation portion, i.e., is positioned on one side of a pair of facing side surfaces. This makes it possible to reduce the moving distance of the microscope, thereby reducing the size of the apparatus and the observation time.

EXAMPLE 4

As Example 4, there will be described an example where culture vessels provided with a heat storage material are used by manual operation with the use of an incubator, instead of an automatic culture step performed by the automatic culture apparatus. In this case, unlike Example 1, flow channel tubes are not connected to each culture vessel. Further, the culture vessel may be a closed-system one or an open-system one. Each culture vessel is contained in a heat storage portion in the incubator. In the case where the culture vessel is taken out from the incubator, the culture vessel is quickly put in the heat insulation portion. Decrease in a temperature of the culture vessels remaining in the incubator is prevented by the heat storage portions even in the case where the culture vessels are exposed to air having a room temperature. A temperature of the taken-out culture vessel is maintained by a hot plate in a state in which a part of the heat insulation portion is removed as necessary, and the culture vessel is observed with the use of a microscope. With this, it is possible to prevent decrease in the temperature of the culture vessel. This is particularly effective in the case where temperature-responsive culture surfaces are used in the culture vessels.

Note that the invention is not limited to the above examples and includes various modification examples. For example, the above examples have been described in detail to understand the invention better, and therefore the invention is not necessarily limited to the examples having all the configurations described above. Apart of a configuration of a certain example can be replaced with a configuration of another example, and a configuration of another example can be added to a configuration of a certain example. Further, another configuration can be added to, removed from, or replaced with a part of the configuration of each example.

Although a case where each of the structures, the functions, the control units, and the like described above is realized in software by preparing programs for realizing a part or all thereof has been described, for example, each of the structures, the functions, the control units, and the like may be realized in hardware by designing a part or all thereof with an integrated circuit.

REFERENCE SIGNS LIST 1 culture vessel portion
2, 1203 flow channel portion
3, 213 rotary valve mechanism
4 cell bottle portion
5 medium bottle portion
6 preheating bottle portion
7 waste fluid bag portion
8 observation portion
9 incubator unit
10 gas supply unit
11 humidification bottle portion
12 control unit
13 control terminal
201 culture vessel
202, 1402 culture vessel base
203 actuator
204 and 205 cell bottle
206, 207 flow channel circuit
208 medium bottle
209 preheating bottle
210 branch portion
211 tube pump
212 electromagnetic valve
214, 215 waste fluid bag
216, 404 gas cylinder
217 gas flow meter
218 humidification bottle
219 air-supply circuit
220 sterilized detachable portion
221 sterilized connection portion
222 multi-branch portion
301 observation hole
302 flow channel tube
303 sterilized detachable portion
400, 509 microscope
401 incubator
402 door
403 monitor
405 desk
406 refrigerator
407 storage
408 flow channel tube
409 small window
501 control device
502 display screen
503 incubator and the like
504 temperature adjustment unit
505 temperature sensor
506 gas supply unit
507 solution holding portion and the like
508 fluid movement control mechanism unit
601 heat insulation portion
602 culture dish
603 temperature-responsive cell culture insert vessel
604 connector
605 heat storage material
606 heat storage material vessel
607 receiving portion
608 window
609 upper-surface heat insulation portion
610, 613 lower-surface heat insulation portion
611 side-surface heat insulation portion
612 upper-surface and side-surface heat insulation portion
614 hinge
701, 1201, 1301, 1401 heat storage portion
801 hot plate
900 transportation vessel
901 holding vessel main body portion
902 holding vessel cover portion
903 heat insulation member
904 environment sensor
905, 906 heat storage material
1001 stage
1202 linear metal
1203 planar metal
1204 bar metal

The invention claimed is:

1. A cell culture apparatus, comprising:
a culture vessel base which is arranged in a culture space and on which a plurality of culture vessels are placed; and
a plurality of heat storage portions for warming the plurality of culture vessels, respectively, each heat storage portion including a heat storage material and a receiving portion to be in contact with a culture vessel placed thereon to conduct heat from the heat storage material to the culture vessel placed thereon;
wherein the plurality of heat storage portions, which are placed on the culture vessel base in the culture space during culture and contains the respective culture vessels, are provided so that at least one storage portion is removable from the culture space.

2. The cell culture apparatus according to claim 1, wherein
the culture vessel base includes a guide portion for allowing the plurality of heat storage portions to be arranged in a predetermined region of the culture space so that culture can be performed in a state in which the culture vessels are contained.

3. The cell culture apparatus according to claim 1, further comprising:
an observation portion for observing the plurality of culture vessels,
wherein the culture vessel base has a U-shape and is provided so that the plurality of placed culture vessels surround the observation portion in a state in which the culture vessel base is arranged in a predetermined region of the culture space.

4. The cell culture apparatus according to claim 3, wherein each culture vessel is eccentrically provided in the heat storage portion to be positioned on the observation portion side of the cell culture apparatus.

5. The cell culture apparatus according to claim 3, wherein the observation portion is movable relative to the plurality of culture vessels for observing the plurality of culture vessels.

6. The cell culture apparatus according to claim 5, wherein the observation portion includes a microscope for observing the plurality of culture vessels.

7. The cell culture apparatus according to claim 1, further comprising
a microscope for observing the plurality of culture vessels,
wherein, in the case where observation is performed with the use of the microscope in the cell culture apparatus, the heat storage portions in a direction in which the microscope approaches are thinner than the heat storage portions in directions other than the direction.

8. The cell culture apparatus according to claim 1, wherein, in the case where at least one of the plurality of heat storage portions which are placed on the culture vessel base during culture and contain the respective culture vessels is taken out from the culture space, a temperature of the culture vessels which are not taken out from the culture vessel base is maintainable.

9. The cell culture apparatus according to claim 1, wherein
the culture vessels other than the culture vessel to be taken out and the heat storage portions containing the respective culture vessels are integrally provided and are integrally removable from the culture space.

10. The cell culture apparatus according to claim 1, further comprising:
a heat insulation portion for, in the case where at least one of the plurality of heat storage portions containing the respective culture vessels is taken out from the culture space, covering an outer circumference of the heat storage portion to be taken out.

11. The cell culture apparatus according to claim 10, wherein the heat storage material is provided between each of the plurality of culture vessels provided with the heat storage material and the corresponding heat insulation portion.

12. The cell culture apparatus according to claim 10, wherein the heat insulation portion includes an upper-surface heat insulation portion, a lower-surface heat insulation portion, and a side-surface heat insulation portion
wherein the upper-surface heat insulation portion covers an upper part of the side-surface heat insulation portion, and the lower-surface heat insulation portion cover a lower part of the side-surface heat insulation portion.

13. The cell culture apparatus according to claim 10, wherein a part of the heat insulation portion is removable; and
wherein the heat storage portion which is exposed by removing the part of the heat insulation portion can be heated.

14. The cell culture apparatus according to claim 13, wherein the culture vessel which is exposed by removing the part of the heat insulation portion includes an optically transparent window through which a biological sample in the culture vessel is observable.

15. The cell culture apparatus according to claim 1, wherein each heat storage portion surrounds the culture vessel which is placed on the receiving portion thereof.

16. The cell culture apparatus according to claim 1, wherein each heat storage portion includes a heat storage portion vessel which contains the heat storage material thereof.

17. The cell culture apparatus according to claim 16, wherein the heat storage portion vessel is made of polycarbonate and the receiving portion is made of metal.

18. The cell culture apparatus according to claim 1, wherein each heat storage portion has a trapezoidal shape and the plurality of heat storage portions are arranged in a circular shape.

19. The cell culture apparatus according to claim 1, wherein each heat storage portion has a pair of side surfaces, and the culture vessel contained in said each heat storage portion is eccentrically provided on one side of the pair of side surfaces.

20. The cell culture apparatus according to claim 19, wherein each heat storage portion has a trapezoidal shape and the plurality of heat storage portions are arranged in a circular shape; and
wherein the culture vessel is eccentric on the side surface which is a short side of the trapezoidal shape.

* * * * *